US007989426B2

(12) United States Patent
Campochiaro et al.

(10) Patent No.: US 7,989,426 B2
(45) Date of Patent: Aug. 2, 2011

(54) SELECTIVE INDUCTION OF APOPTOSIS TO TREAT OCULAR DISEASE BY EXPRESSION OF PEDF

(75) Inventors: Peter A. Campochiaro, Baltimore, MD (US); Peter Gehlbach, Hunt Valley, MD (US)

(73) Assignee: Johns Hopkins University School of Medicine, Baltimore, MD (US)

( * ) Notice: Subject to any disclaimer, the term of this patent is extended or adjusted under 35 U.S.C. 154(b) by 617 days.

(21) Appl. No.: 11/938,562

(22) Filed: Nov. 12, 2007

(65) Prior Publication Data

US 2008/0132464 A1 Jun. 5, 2008

Related U.S. Application Data

(60) Division of application No. 11/377,857, filed on Mar. 16, 2006, now abandoned, which is a continuation of application No. 10/367,038, filed on Feb. 14, 2003, now abandoned.

(60) Provisional application No. 60/357,340, filed on Feb. 15, 2002.

(51) Int. Cl.
*A61K 48/00* (2006.01)
*A01N 63/00* (2006.01)

(52) U.S. Cl. ..................................... 514/44 R; 424/93.2

(58) Field of Classification Search ........................ None
See application file for complete search history.

(56) References Cited

U.S. PATENT DOCUMENTS

| 4,405,712 | A | 9/1983 | Vande Woude |
|---|---|---|---|
| 4,497,796 | A | 2/1985 | Salser et al. |
| 4,727,028 | A | 2/1988 | Santerre et al. |
| 4,740,463 | A | 4/1988 | Weinberg et al. |
| 5,190,931 | A | 3/1993 | Inouye |
| 5,208,149 | A | 5/1993 | Inouye |
| 5,518,913 | A | 5/1996 | Massie et al. |
| 5,583,009 | A | 12/1996 | Palmiter et al. |
| 5,641,749 | A | 6/1997 | Yan et al. |
| 5,710,136 | A | 1/1998 | Robinson et al. |
| 5,770,580 | A | 6/1998 | Ledley et al. |
| 5,792,751 | A | 8/1998 | Ledley et al. |
| 5,801,156 | A | 9/1998 | Robinson et al. |
| 5,824,544 | A | 10/1998 | Armentano et al. |
| 5,827,702 | A | 10/1998 | Cuthbertson |
| 5,840,686 | A | 11/1998 | Chader et al. |
| 5,851,806 | A | 12/1998 | Kovesdi et al. |
| 5,891,690 | A | 4/1999 | Massie et al. |
| 5,962,311 | A | 10/1999 | Wickham et al. |
| 5,994,106 | A | 11/1999 | Kovesdi et al. |
| 6,113,913 | A | 9/2000 | Brough et al. |
| 6,168,941 | B1 | 1/2001 | Liu |
| 6,204,251 | B1 | 3/2001 | Cuthbertson |
| 6,225,113 | B1 | 5/2001 | Brough et al. |
| 6,228,646 | B1 | 5/2001 | Hardy |
| 6,288,024 | B1 | 9/2001 | Bouck et al. |
| 6,410,298 | B1 | 6/2002 | Crouzet et al. |
| 2002/0064870 | A1 | 5/2002 | Briand et al. |
| 2002/0168342 | A1 | 11/2002 | Wang et al. |
| 2003/0158112 | A1 | 8/2003 | Campochiaro |

FOREIGN PATENT DOCUMENTS

| AU | 95/28533 A | 3/1996 |
|---|---|---|
| AU | 95/38477 B2 | 5/1996 |
| AU | 2000/31294 B2 | 12/2000 |
| CA | 2053187 A1 | 4/1993 |
| CA | 2117668 A1 | 9/1995 |
| EP | 1083229 A1 | 3/2001 |
| FR | 2707664 A1 | 1/1995 |
| FR | 2718749 A1 | 10/1995 |
| WO | WO 93/24529 A | 12/1993 |
| WO | WO 94/01139 A | 1/1994 |
| WO | WO 94/08026 A | 4/1994 |
| WO | WO 94/11506 A | 5/1994 |
| WO | WO 94/12649 A | 6/1994 |
| WO | WO 94/20146 A | 9/1994 |
| WO | WO 94/24297 A | 10/1994 |
| WO | WO 94/26914 A | 11/1994 |
| WO | WO 94/28152 A | 12/1994 |
| WO | WO 94/28938 A | 12/1994 |
| WO | WO 95/00655 A | 1/1995 |
| WO | WO 95/16722 A | 6/1995 |
| WO | WO 95/19182 A | 7/1995 |
| WO | WO 95/26411 A | 10/1995 |
| WO | WO 95/27071 A | 10/1995 |
| WO | WO 95/33480 A | 12/1995 |
| WO | WO 95/34671 A | 12/1995 |

(Continued)

OTHER PUBLICATIONS

Stellmach, et al. (2001) Proceedings of the National Academy of Science, USA., 98(5): 2593-97.* Demetriades, et al. (2008) Journal of Ocular Pharmacology and Therapeutics, 42(1): 70-79.*
Aiello et al., "Suppression of retinal neovascularization in vivo by inhibition of vascular endothelial growth factor (VEGF) using soluble VEGF-receptor chimeric proteins," *Proc. Natl. Acad. Sci. USA*, 92 (23): 10457-10461 (Nov. 1995).
Amalfitano et al., "Production and characterization of improved adenovirus vectors with E1, E2b, and E3 genes deleted," *J. Virol.*, 72 (2): 926-933 (Feb. 1998).
Armentano et al., "Characterization of an adenovirus gene transfer vector containing an E4 deletion," *Hum. Gene Ther.*, 6: 1343-1353 (Oct. 1995).

(Continued)

*Primary Examiner* — Robert M Kelly
(74) *Attorney, Agent, or Firm* — Leydig, Voit & Mayer, Ltd.

(57) ABSTRACT

The invention is directed to a method of prophylactically or therapeutically treating choroidal neovascularization, wherein the method comprises directly administering to the eye a therapeutic factor or a nucleic acid sequence that encodes a therapeutic factor, which he expressed to produce the therapeutic factor, to selectively induce apoptosis of endothelial cells associated with neovascularization of the choroid such that choroidal neovascularization is treated prophylactically or therapeutically. The invention also provides a method of prophylactically or therapeutically treating ocular neovascularization, wherein the method comprises directly administering to the eye a nucleic acid sequence encoding a therapeutic factor to promote apoptosis of endothelial cells associated with neovascularization, such that the nucleic acid is expressed thereby producing the therapeutic factor to treat ocular neovascularization prophylactically or therapeutically.

10 Claims, No Drawings

FOREIGN PATENT DOCUMENTS

| | | |
|---|---|---|
| WO | WO 96/13276 A | 5/1996 |
| WO | WO 96/14061 A | 5/1996 |
| WO | WO 96/18418 A | 6/1996 |
| WO | WO 97/21826 A | 6/1997 |
| WO | WO 97/37542 A | 10/1997 |
| WO | WO 97/47307 A | 12/1997 |
| WO | WO 98/49321 A | 11/1998 |
| WO | WO 99/04806 A | 2/1999 |
| WO | WO 99/16889 A | 4/1999 |
| WO | WO 99/25861 A | 5/1999 |
| WO | WO 99/26480 A | 6/1999 |
| WO | WO 99/29345 A | 6/1999 |
| WO | WO 00/15822 A | 3/2000 |
| WO | WO 00/52479 A | 9/2000 |
| WO | WO 00/54813 A | 9/2000 |
| WO | WO 01/44280 A | 6/2001 |
| WO | WO 02/24234 A | 3/2002 |

OTHER PUBLICATIONS

Auricchio et al., "Pharmacological regulation of protein expression from adeno-associated viral vectors in the eye," *Mol. Ther.*, 6 (2): 238-242 (Aug. 2002).

Baffi et al., "Choroidal neovascularization in the rat induced by adenovirus mediated expression of vascular endothelial growth factor," *Invest. Ophthalmol. Visual Sci.*, 41 (11): 3582-3589 (Oct. 2000).

Bainbridge et al., "Gene therapy for ocular angiogenesis," *Clin. Sci.*, 104: 561-575 (2003).

Barr et al., "Efficient catheter-mediated gene transfer into the heart using replication-defective adenovirus," *Gene Ther.*, 1: 51-58 (1994).

Benihoud et al., "Adenovirus vectors for gene therapy," *Curr. Opin. Biotechnol.*, 10: 440-447 (1999).

Berkner et al., "Abundant expression of polyomavirus middle T antigen and dihydrofolate reductase in an adenovirus recombinant," *J. Virol.*, 61 (4): 1213-1220 (Apr. 1987).

Berkner et al., "Generation of adenovirus by transfection of plasmids," *Nucl. Acids Res.*, 11 (17): 6003-6020 (1983).

Berkner, "Development of adenovirus vectors for the expression of heterologous genes," *BioTechniques*, 6 (7): 616-629 (1988).

Boucher et al., "Gene therapy for cystic fibrosis using E1-deleted adenovirus: A phase I trial in the nasal cavity," *Hum. Gene Ther.*, 5: 615-639 (1994).

Brough et al. "Multiple functions of the adenovirus DNA-binding protein are required for efficient viral DNA synthesis," *Virol.*, 196: 269-281 (1993).

Brough et al., "A gene transfer vector-cell line system for complete functional complementation of adenovirus early regions E1 and E4," *J. Virol.*, 70 (9): 6497-6501 (Sep. 1996).

Brough et al., "Construction, characterization, and utilization of cell lines which inducibly express the adenovirus DNA-binding protein," *Virology*, 190: 624-634 (1992).

Chen et al., "Reactivation of silenced, virally transduced genes by inhibitors of histone deacetylase," *Proc. Natl. Acad. Sci USA*, 94: 5798-2803 (May 1997).

Chen et al., "The activation of trans-acting factors in response to hypo- and hyper-osmotic stress in mammalian cells," in *Environmental Stressors and Gene Responses* (Storey et al., eds): 141-155 (Elsevier Science Ltd., Amsterdam, Netherlands, Jan. 2000).

Crystal et al., "Administration of an adenovirus containing the human CFTR cDNA to the respiratory tract of individuals with cystic fibrosis," *Nat. Genet.*, 8, 42-51 (Sep. 1994).

Crystal, "Transfer of genes to humans: Early lessons and obstacles to success," *Science*, 270: 404-410 (Oct. 20, 1995).

Davidson et al., "Overproduction of polyomavirus middle T antigen in mammalian cells through the use of an adenovirus vector," *J. Virol.*, 61 (4): 1226-1239 (Apr. 1987).

Dawson et al., "Pigment epithelium-derived factor: A potent inhibitor of angiogenesis," *Science*, 285 (5425): 245-248 (Jul. 9, 1999).

Dejneka et al., "Pharmacologically regulated gene expression in the retina following transduction with viral vectors," *Gene Ther.*, 8 (6): 442-446 (Mar. 2001).

Deonarain, "Ligand-targeted receptor-mediated vectors for gene delivery," *Exp. Opin. Ther. Pat.*, 8 (1): 53-69 (1998).

Eck et al., in *The Pharmacological Basis of Therapeutics, 9th Ed.* (Goodman et al., eds.): 77-101 (McGraw Hill, New York, NY 1996).

Engelhardt et al., "Ablation of *E2A* in recombinant adenoviruses improves transgene persistence and decreases inflammatory response in mouse liver," *Proc. Natl. Acad. Sci. USA*, 91: 6196-6200 (Jun. 1994).

Engelhardt et al., "Adenovirus-mediated transfer of the CFTR gene to lung of nonhuman primates: Biological efficacy study," *Hum. Gene Ther.*, 4: 759-769 (1993).

Fallaux et al., "Characterization of 911: A new helper cell line for the titration and propagation of early region 1-deleted adenoviral vectors," *Hum. Gene Ther.*, 7: 215-222 (Jan. 20, 1996).

Gaetano et al., "Transcriptionally active drugs improve adenovirus vector performance in vitro and in vivo," *Gene Ther.*, 7 (19): 1624-1630 (Oct. 2000).

Gao et al., "A cell line for high-yield production of E1-deleted adenovirus vectors without the emergence of replication-competent virus," *Hum. Gene Ther.*, 11: 213-219 (Jan. 1, 2000).

Gehlbach et al., "Periocular injection of an adenoviral vector encoding pigment epithelium-derived factor inhibits choroidal neovascularization," *Gene Ther.*, 10: 637-646 (2003).

Gilardi et al., "Expression of human $\alpha_1$-antitrypsin using a recombinant adenovirus vector," *FEBS Lett.*, 267 (1): 60-62 (Jul. 1990).

Górecki, "Prospects and problems of gene therapy: an update," *Exp. Opin. Emerging Drugs*, 6 (2): 187-198 (2001).

Graham et al., "Characteristics of a human cell line transformed by DNA from human adenovirus type 5," *J. Gen. Virol.*, 36 (1): 59-72 (Jul. 1977).

Gura, "Systems for identifying new drugs are often faulty," *Science*, 278: 1041-1042 (Nov. 7, 1997).

Hehir et al., "Molecular characterization of replication-competent variants of adenovirus vectors and genome modifications to prevent their occurrence," *J. Virol.*, 70 (12): 8459-8467 (Dec. 1996).

Imler et al., "Novel complementation cells derived from human lung carcinoma A549 cells support the growth of E1-deleted adenovirus vectors," *Gene Ther.*, 3: 75-84 (1996).

Kaplan, "Fas-Ligand (CD 95 ligand) controls angiogenesis beneath the retina," *Nature Med.*, 5 (3): 292-297 (1999).

Kendall et al., "Inhibition of vascular endothelial cell growth factor activity by an endogenously encoded soluble receptor," *Proc. Natl. Acad. Sci. USA*, 90 (22): 10705-10709 (Nov. 1993).

Kim et al., "Hypoosmotic stress activates nuclear factor-κB in primary rat hepatocytes: Implications in cell cycle progression," *Surg. Forum*, 50: 21-23 (1999).

Klessig et al., "Introduction, stable integration, and controlled expression of a chimeric adenovirus gene whose product is toxic to the recipient human cell," *Mol. Cell. Biol.*, 4 (7): 1354-1362 (Jul. 1984).

Kreeger, "Hot Papers: Gene Therapy," *The Scientist*, 10 (4) (Feb. 19, 1996).

Krougliak et al., "Development of cells lines capable of complementing E1, E4, and Protein IX defective adenovirus type 5 mutants," *Hum. Gene Ther.*, 6: 1575-1586 (Dec. 1995).

Lai et al., "Inhibition of angiogenesis by adenovirus-mediated sFlt-1 expression in a rat model of corneal neovascularization," *Hum. Gene Ther.*, 12 (10): 1299-1310 (Jul. 1, 2001).

Lambert et al., "Influence of plasminogen activator inhibitor type 1 on choroidal neovascularization," *FASEB J.*, 15: 1021-1027 (Apr. 2001).

Lemarchand et al., "Adenovirus-mediated transfer of a recombinant human $\alpha 1$-antitrypsin cDNA to human endothelial cells," *Proc. Natl. Acad. Sci. USA*, 89: 6482-6486 (Jul. 15, 1992).

Lochmüller et al., "Emergence of an early region 1-containing replication-competent adenovirus in stocks of replication-defective adenovirus recombinants ($\Delta$E1+$\Delta$E3) during multiple passages in 293 cells," *Hum. Gene Ther.*, 5: 1485-1491 (Dec. 1994).

Löser et al., "Reactivation of the previously silenced cytomegalovirus major immediate-early promoter in the mouse liver: Involvement of NfκB," *J. Virol.*, 72 (1): 180-190 (Jan. 1998).

Ma et al., "Treatment of retinal edema using peptide angiogenic inhibitors," *BIOSIS*, Accession No. PREV200300538899 (*ARVO Annual Meeting*, Abstract No. 4029 (Fort Lauderdale, FL USA, May 4-8, 2003)).

Mansour et al., "Downstream sequences affect transcription initiation from the adenovirus major late promoter," *Mol. Cell Biol.*, 6 (7): 2684-2694 (Jul. 1986).

Mashour et al., "In vivo adenovirus-mediated gene transfer into ocular tissues," *Gene Ther.*, 1 (2): 122-126 (1994).

Mastrangeli et al., "Diversity of airway epithelial cell targets for in vivo recombinant adenovirus-mediated gene transfer," *J. Clin. Invest.*, 91: 225-234 (Jan. 1993).

McGrory et al., "A simple technique for the rescue of early region I mutations into infectious human adenovirus type 5," *Virology*, 163: 614-617 (1988).

McVey et al., "Adenoviral gene delivery for the treatment of ocular diseases," *BIOSIS*, Accession No. PREV200300511852 (*ARVO Annual Meeting*, Abstract No. 444 (Fort Lauderdale, FL USA, May 4-8, 2003)).

Mittereder et al., "Evaluation of the efficacy and safety of in vitro, adenovirus-mediated transfer of the human cystic fibrosis transmembrane conductance regulator cDNA," *Hum. Gene Ther.*, 5: 771-729 (1994).

Mori et al., "AAV-mediated gene transfer of pigment epithelium-derived factor inhibits choroidal neovascularization," *BIOSIS*, Accession No. PREV200200379191 (*IOVS*, 43 (6): 1194-2000 (Jun. 2002)).

Mori et al., "Pigment epithelium-derived factor inhibits retinal and choroidal neovascularization," *J. Cell. Physiol.*, 188 (2): 253-263 (Aug. 2001).

Mori et al., "Regression of ocular neovascularization in response to increased expression of pigment epithelium-derived factor," *Invest. Ophthalmol. Vis. Sci.*, 43 (7): 2428-2434 (Jul. 2002).

Morin et al., "Nuclear localization of the adenovirus DNA-binding protein: Requirement for two signals and complementation during viral infection," *Mol. Cell. Biol.*, 9 (10): 4372-4380 (Oct. 1989).

Pignolo et al., "Senescent WI-38 cells fail to express EPC-1, a gene induced in young cells upon entry into the G0 state," *J. Biol. Chem.*, 268 (12): 8949-8957 (Apr. 25, 1993).

Raisler et al., "AAV-mediated expression of PEDF or angiostatin (K1K3) reduces retinal neovascularization in a mouse model of ischemic retinopathy," *BIOSIS*, Accession No. PREV200300143029 (*ARVO Annual Meeting*, Abstract No. 1258 (Fort Lauderdale, FL USA, May 5-10, 2002)).

Ramussen et al., "Looking into anti-angiogenic genet herapies for disorders of the eye," *Drug Discov. Today*, 6 (22): 1171-1175 (Nov. 2001).

Rosenfeld et al., "In vivo transfer of the human cystic fibrosis tarnsmembrane conductance regulator gene to the airway epithelium," *Cell*, 68: 143-158 (Jan. 10, 1992).

Salti et al., "Diabetes-induced retinal vascular permeability is reversed by intravitreal injection of pigment epithelial derived factor," *BIOSIS*, Accession No. PREV200300165296 (*ARVO Annual Meeting*, Abstract No. 3864 (Fort Lauderdale, FL USA, May 5-10, 2002)).

Schaack et al., "Adenovirus type 5 precursor terminal protein-expressing 293 and HeLa cell lines," *J. Virol.*, 69: 4079-4085 (Jul. 1995).

Simon et al., "Adenovirus-mediated transfer of the CFTR gene to lung of nonhuman primates: Toxicity study," *Hum. Gene Ther.*, 4, 771-780 (1993).

Steele et al., "Pigment epithelium-derived factor: neurotrophic activity and identification as a member of the serine protease inhibitor gene family," *Proc. Natl. Acad. Sci. USA*, 90 (4): 1526-1530 (Feb. 1992).

Trapnell et al., "Gene therapy using adenoviral vectors," *Curr. Opin. Biotechnol.*, 5: 617-625 (1994).

Verma et al., "Gene therapy—promises, problems and prospects," *Nature*, 389: 239-242 (1997).

Vos et al., "Characterization of adenovirus type 5 insertion and deletion mutants encoding altered DNA binding proteins," *Virology*, 172: 634-642 (1989).

Wang et al., "A packaging cell line for propagation of recombinant adenovirus vectors containing two lethal gene-region deletions," *Gene Ther.*, 2: 775-783 (1995).

Weinberg et al., "A cell line that supports the growth of a defective early region 4 deletion mutant of human adenovirus type 2," *Proc. Natl. Acad. Sci. USA*, 80: 5383-86 (Sep. 1983).

Yang et al., "Cellular immunity to viral antigens limits E1-deleted adenoviruses for gene therapy," *Proc. Natl. Acad. Sci. USA*, 91: 4407-4411 (May 1994).

Yang et al., "Inactivation of *E2a* in recombinant adenoviruses improves the prospect for gene therapy in cystic fibrosis," *Nat. Genet.*, 7, 362-369 (Jul. 1994).

Yeh et al., "Efficient dual transcomplementation of adenovirus E1 and E4 regions from a 293-derived cell line expressing a minimal E4 functional unit," *J. Virol.*, 70 (1): 559-565 (Jan. 1996).

Zhou et al., "Progress towards development of an adenoviral vector with deletions of E1 and E2a," *J. Cell. Biochem., Supp. 21A*: 434 (1995).

Zhu et al., "Characterization of replication-competent adenovirus isolates from large-scale production of a recombinant adenoviral vector," *Hum. Gene Ther.*, 10: 113-121 (Jan. 1, 1999).

Campochiaro, Retinal and Choroidal Neovascularization, *Journal of Cellular Physiology*, 814:301-310 (2000).

\* cited by examiner

SELECTIVE INDUCTION OF APOPTOSIS TO TREAT OCULAR DISEASE BY EXPRESSION OF PEDF

CROSS-REFERENCE TO RELATED APPLICATIONS

This patent application is a divisional of U.S. patent application Ser. No. 11/377,857, filed Mar. 16, 2006, now abandoned, which is a continuation of U.S. patent application Ser. No. 10/367,038, filed Feb. 14, 2003, now abandoned, which claims the benefit of U.S. Provisional Patent Application No. 60/357,340, filed Feb. 15, 2002.

FEDERALLY SPONSORED RESEARCH AND DEVELOPMENT

This invention was made in part with Government support under Grant Numbers EYO5951, EYO12609, and K08 awarded by the National Eye Institute, National Institutes of Health. The Government may have certain rights in this invention.

FIELD OF THE INVENTION

The invention relates to a method of prophylactically or therapeutically treating an ocular disorder associated with abnormal neovascularization.

BACKGROUND OF THE INVENTION

An overwhelming majority of the world's population will experience some degree of vision loss in their lifetime. Vision loss affects virtually all people regardless of age, race, economic or social status, or geographical location. Ocular-related disorders, while often not life threatening, necessitate life-style changes that jeopardize the independence of the afflicted individual. Vision impairment can result from most all ocular disorders, including diabetic retinopathies, proliferative retinopathies, retinal detachment, toxic retinopathies, retinal vascular diseases, retinal degenerations, vascular anomalies, age-related macular degeneration and other acquired disorders, infectious diseases, inflammatory diseases, ocular ischemia, pregnancy-related disorders, retinal tumors, choroidal tumors, choroidal disorders, vitreous disorders, trauma, cataract complications, dry eye, and inflammatory optic neuropathies.

Leading causes of severe vision loss and blindness are ocular-related disorders wherein the vasculature of the eye is damaged or insufficiently regulated. Ocular-related diseases comprising a neovascularization complication are many and include, for example, exudative age-related macular degeneration, diabetic retinopathy, corneal neovascularization, choroidal neovascularization, cyclitis, Hippel-Lindau Disease, retinopathy of prematurity, pterygium, histoplasmosis, iris neovascularization, macular edema, glaucoma-associated neovascularization, and the like. It is likely that severe vision loss does not result directly from neovascularization, but the effect of neovascularization on the retina. The retina is a delicate ocular membrane on which images are received. Near the center of the retina is the macula lutea, an oval area of retinal tissue where visual sense is most acute. The retina is most delicate at the fovea centralis, the central depression located in the center of the macula. Damage of the retina, i.e., retinal detachment, retinal tears, or retinal degeneration, is directly connected to vision loss. A common cause of retinal detachment, retinal tears, and retinal degeneration is abnormal, i.e., uncontrolled, vascularization of various ocular tissues, although a small percentage of cases are due to atrophic complications. Disorders associated with both neovascular and atrophic components, such as age-related macular degeneration and diabetic retinopathy, are particularly difficult to treat due to the emergence of a wide variety of complications.

Age-related macular degeneration (AMD) is the leading cause of blindness in patients over 65 years of age. As the elderly population of the world increases, the incidence of age-related macular degeneration is expected to increase dramatically, reaching a predicted 7.5 million cases in the United States alone by the year 2030 (Hyman et al., *Am. J. Epidemiol.*, 118, 213-227 (1983)). Age-related macular degeneration is a progressive, degenerative disorder of the eye resulting initially in loss of visual acuity. Many patients afflicted with AMD experience exudative complications, including disciform scars (i.e., scarring involving fibrous elements) and neovascularization. Severe vision loss occurs as neovascularization or atrophy disturbs the foveal center (Bressler et al., *Opthalmology*, 102, 1206-1211 (1995)). Ultimately, legal blindness from age-related macular degeneration stems from degeneration of the RPE and the subsequent death of photoreceptors.

Like AMD, diabetic retinopathy is subdivided into a non-proliferative stage, which typically occurs first, and a proliferative stage. The proliferative stage of diabetic retinopathy is characterized by neovascularization and fibrovascular growth (i.e., scarring involving glial and fibrous elements) from the retina or optic nerve over the inner surface of the retina or disc or into the vitreous cavity.

Abnormal vascularization of the eye also can occur in the layer directly underneath the retina, i.e., the choroid. Choroidal neovascularization (CNV) is often associated with AMD and results in leakage, bleeding, and scarring in the macula. Scarring in the macula results in a central scotoma (interruption of the visual field) and loss of reading and driving vision. Choroidal neovascularization is detected using angiography, e.g., fluorescein angiography, alone or in combination with indocyanine-green angiography.

For many ocular-related disorders, there are currently no effective therapeutic options. Laser photocoagulation, the administration of laser burns to various areas of the eye, is used in the treatment of many neovascularization-linked disorders. For example, focal macular photocoagulation is used to treat areas of vascular leakage in the macula (Murphy, *Amer. Family Physician*, 51(4), 785-796 (1995)). Similarly, neovascularization, in particular, advanced proliferative retinopathy, is commonly treated with scatter or panretinal photocoagulation. However, laser treatment may cause permanent blind spots corresponding to the treated areas. With respect to age-related macular degeneration, many patients eventually experience severe vision loss in spite of treatment. Other treatment options for ocular-related disorders include thermotherapy, photodynamic therapy, radiation therapy, and surgery to either translocate the macula or remove the abnormal blood vessels. However, only photodynamic therapy and focal laser have been found to be better than no treatment at all, and the treatment effect is marginal and temporary.

Given the prevalence of ocular-related disorders and the lack of effective treatments, there remains a need for an effective prophylactic and therapeutic treatment of ocular-related disorders, in particular ocular-related disorders with complications associated with abnormal cellular proliferation (e.g., neovascularization), such as diabetic retinopathy, age-related macular degeneration, and choroidal neovascularization. Accordingly, the invention provides materials and methods for prophylactically and therapeutically treating disorders associated with neovascularization, in particular, ocular-related disorders associated with neovascularization. This and other advantages of the invention will become apparent from the detailed description provided herein.

BRIEF SUMMARY OF THE INVENTION

The invention provides a method for the prophylactic or therapeutic treatment of ocular-related disorders. In particular, the invention provides a method of prophylactically or therapeutically treating neovascularization in the eye, e.g., choroidal neovascularization. The method comprises directly administering a therapeutic factor, or administering a nucleic acid sequence encoding a therapeutic factor, which is expressed to produce the therapeutic factor, to the eye to selectively induce apoptosis of endothelial cells associated with neovascularization, thereby treating the ocular disease prophylactically or therapeutically. Preferably, the therapeutic factor is an inhibitor of angiogenesis or a neurotrophic agent. More preferably, the therapeutic factor comprises both anti-angiogenic and neurotrophic activity, such as PEDF.

DETAILED DESCRIPTION OF THE INVENTION

The invention is directed to a method of prophylactically or therapeutically treating an animal, preferably a mammal (e.g., a human), for at least one ocular-related disorder associated with neovascularization. Ocular-related disorders appropriate for treatment using the inventive method include, but are not limited to, diabetic retinopathies, proliferative retinopathies, retinopathy of prematurity, retinal vascular diseases, vascular anomalies, age-related macular degeneration and other acquired disorders, endophthalmitis, infectious diseases, inflammatory diseases, AIDS-related disorders, ocular ischemia syndrome, pregnancy-related neovascular disorders, peripheral retinal degenerations, retinal degenerations with neovascular complications, toxic retinopathies, retinal tumors, corneal neovascularization, choroidal tumors, choroidal disorders, choroidal neovascularization, neovascular glaucoma, vitreous disorders, retinal detachment and proliferative vitreoretinopathy associated with neovascularization, macular edema, iris neovascularization, neovascularization associated with severe myopia, surgical-induced neovascular disorders, and the like, which are not mutually exclusive.

In particular, the invention provides a method of prophylactically or therapeutically treating an animal for ocular neovascularization. The method comprises directly administering a therapeutic factor or a nucleic acid sequence encoding a therapeutic factor to the eye to selectively induce apoptosis of endothelial cells associated with neovascularization. When the method comprises contacting an ocular cell with a nucleic acid sequence encoding the therapeutic factor, the nucleic acid sequence is expressed to produce the therapeutic factor to prophylactically or therapeutically treat ocular neovascularization. By "directly administering to the eye" is meant that the nucleic acid sequence contacts cells on, within, and surrounding the globe of the eye. In other words, the nucleic acid sequence can contact cells associated with the globe of the eye, such as, but not limited to, cells on the surface of the eye (e.g., conjunctival cells), or cells that make up the inner layers of the eye (e.g., cells of the retinal or choriodal layers). The nucleic acid sequence also can contact cells of the ocular apparatus such as, but not limited to, ocular muscle cells, cells lining the ocular orbital, fibroblasts, and the like. The therapeutic factor is produced in the cells of the ocular apparatus and penetrates the globe of the eye to exert a biological effect on endothelial cells, directly or indirectly.

Desirably, the therapeutic factor is an inhibitor of angiogenesis (e.g., via apoptosis of appropriate cells) or a neurotrophic agent. Most preferably, the therapeutic factor comprises both anti-angiogenic and neurotrophic activities.

The inventive method is superior over previously described methods of treating neovascularization via destruction of the cells associated with neovascularization in that the inventive method selectively kills endothelial cells associated with new vascular structures, thereby minimizing harm to existing vasculature within the eye. While neovascularization throughout the body has common features, each area of neovascularization also comprises unique characteristics. Indeed, it has been proven that neovascular processes in different vascular beds of the same organ show overlapping, but not identical characteristics. In addition, it has been demonstrated that newly formed blood vessels and established blood vessels differ with respect to factors required for persistence of the vessels (Campochiaro, *J. Cell. Phys.,* 184, 301-310 (2000)). Thus, it is possible to capitalize on the distinctions between neovascular processes and established blood vessels to selectively ablate cells associated with new blood vessel growth, thereby prophylactically or therapeutically treating ocular disorders associated with neovascularization. The therapeutic factor of the inventive method selectively induces apoptosis of cells associated with neovascularization compared to cells associated with existing vasculature. Desirably, apoptosis is selectively induced in endothelial cells associated with uncontrolled or abnormal angiogenesis. By "selectively inducing apoptosis" is meant that apoptosis induced by the therapeutic factor in cells associated with neovascularization is at least about five times greater than apoptosis induced by the therapeutic factor in cells associated with existing vasculature. More preferably, the level of apoptosis in cells associated with neovascularization (e.g., endothelial cells) induced by the therapeutic factor is at least about 5-times greater, preferably at least about 10-times greater (e.g., at least about 15-times greater, at least about 20-times greater, at least about 30-times greater) than the level of apoptosis induced by the therapeutic factor in cells associated with existing vasculature. Even more preferably, apoptosis in neovascular cells is at least about 50-times greater than the level of apoptosis in cells of existing vasculature when apoptosis is induced by the therapeutic factor. Most preferably, the therapeutic factor does not induce apoptosis in cells of existing vasculature (i.e., blood vessels present before the onset of diseased neovascularization).

The ocular neovascularization treated by the inventive method can be neovascularization associated with any region of the eye. Preferably the neovascularization is neovascularization of the choroid. The choroid is a thin, vascular membrane located under the retina. Abnormal neovascularization of the choroid results from, for example, age-related macular degeneration, histoplasmosis, myopic degeneration, angioid streaks, choroidal rupture, photocoagulation, or any disease that results in a choroidal scar or break in Bruch's membrane such as, for example, Best's disease, choroidal hemangioma, metallic intraocular foreign body, choroidal nonperfusion, choroidal osteomas, bacterial endocarditis, choroideremia, chronic retinal detachment, drusen, deposit of metabolic waste material, endogenous *Candida* endophthalmitis, neovascularization at ora serrata, operating microscope burn, punctate inner choroidopathy, radiation retinopathy, retinal cryoinjury, retinitis pigmentosa, retinochoroidal coloboma, rubella, subretinal fluid drainage, tilted disc syndrome, *Toxoplasma* retinochoroiditis, tuberculosis, and the like. When the inventive method is used to treat or prevent choroidal neovascularization, apoptosis of endothelial cells of the neovasculature of the choroid is sought, with little, if any, apoptosis of endothelial cells associated with existing vasculature of the choroid or the retina.

Neovascularization of the cornea is also appropriate for treatment by the method of the invention. The cornea is a projecting, transparent section of the fibrous tunic, which is the outer most layer of the eye. The outermost layer of the cornea contacts the conjunctiva, while the innermost layer comprises the endothelium of the anterior chamber. Corneal neovascularization stems from, for example, ocular injury, surgery, infection, improper wearing of contact lenses, and diseases such as, for example, corneal dystrophies.

Alternatively, the ocular neovascularization is neovascularization of the retina. Retinal neovascularization is an indication associated with numerous ocular diseases and disorders, many of which are named above. Preferably, the neovascularization of the retina treated in accordance with the inventive method is associated with diabetic retinopathy. Common causes of retinal neovascularization include ischemia, viral infection, and retinal damage. Neovascularization of the retina can lead to macular edema, subretinal discoloration, scarring, and the like. Complications associated with retina neovascularization stem from breakage and leakage of newly formed blood vessels. Vision is impaired as blood fills the vitreous cavity and is not efficiently removed. Not only is the passage of light impeded, but an inflammatory response to the excess blood and metabolites can cause further damage to ocular tissue. Thus, the inventive method can protect against macular edema by inhibiting the formation of leaky diseased neovasculature. In addition, the new vessels form fibrous scar tissue, which, over time, will disturb the retina causing retinal tears and detachment. In addition, vision is impaired by the subsequent damage or destruction of photoreceptors.

The method of the invention also is useful in prophylactically or therapeutically treating an animal for age-related macular degeneration associated with at least one exudative complication. Exudative complications include, for example, disciform scars (i.e., scarring involving fibrous elements) and neovascularization. Prophylactic and therapeutic treatment of age-related macular degeneration is further discussed in, for example, International Patent Application WO 01/58494.

An embodiment of the invention provides a method for prophylactically or therapeutically treating an animal for choroidal neovascularization. The method comprises directly administering to the eye a therapeutic factor or a nucleic acid sequence encoding the therapeutic factor that selectively induces apoptosis of endothelial cells associated with choroidal neovascularization. Preferably, the existing vascularization of the eye is not affected. In that a great deal of damage occurs as a result of edema, thickening of underlying membranes, and build-up of metabolic byproducts, preferably the nucleic acid sequence encoding the therapeutic factor (or the therapeutic factor itself) is administered to an area of vascular leakage or an area adjacent to vascular leakage.

By "prophylactic" is meant the protection, in whole or in part, against ocular neovascularization. By "therapeutic" is meant the amelioration of ocular neovascularization, itself, and, desirably, the protection, in whole or in part, against further ocular neovascularization. One of ordinary skill in the art will appreciate that any degree of protection from, or amelioration of, ocular neovascularization is beneficial to a patient. The invention is particularly advantageous in that the therapeutic factor is directly applied to affected areas without some of the harmful side effects of many presently employed therapies.

The inventive method is useful in the treatment of both acute and persistent, progressive ocular neovascularization. For acute ailments, the therapeutic factor or the nucleic acid sequence encoding the therapeutic factor can be administered using a single or multiple applications within a short time period. If neovascularization persists, numerous applications of the therapeutic factor may be necessary to realize a therapeutic effect.

The therapeutic factor, which in most cases will comprise a protein or peptide with therapeutic activity, can be delivered to the eye in a pharmaceutically-acceptable carrier. Ideally, the therapeutic factor is administered directly to the eye to minimize transmission of the therapeutic factor to non-target tissues. Alternatively, a nucleic acid sequence encoding the therapeutic factor can be delivered to the eye where it is expressed. The produced therapeutic factor is thereby administered to target ocular cells.

Preferably, a nucleic acid sequence encoding the therapeutic factor is directly administered to the eye. Ideally, the nucleic acid sequence is incorporated into an expression vector. Any of a number of expression vectors known in the art and able to transduce ocular cells is suitable for use in the inventive methods. Examples of suitable expression vectors include, for instance, plasmids, plasmid-liposome complexes, and viral vectors, e.g., parvoviral-based vectors (i.e., adeno-associated virus (AAV)-based vectors), retroviral vectors, herpes simplex virus (HSV)-based vectors, AAV-adenoviral chimeric vectors, and adenovirus-based vectors. These expression vectors can be prepared using standard recombinant DNA techniques described in, e.g., Sambrook et al., *Molecular Cloning, a Laboratory Manual*, 2d edition, Cold Spring Harbor Press, Cold Spring Harbor, N.Y. (1989), and Ausubel et al., *Current Protocols in Molecular Biology*, Greene Publishing Associates and John Wiley & Sons, New York, N.Y. (1994).

Plasmids, genetically engineered circular double-stranded DNA molecules, can be designed to contain an expression cassette for delivery of the nucleic acid sequence encoding at least one inhibitor of angiogenesis and/or at least one neurotrophic factor to an ocular cell. Although plasmids were the first vector described for administration of therapeutic nucleic acids, the level of transfection efficiency is poor compared with other techniques. By complexing the plasmid with liposomes, the efficiency of gene transfer in general is improved. While the liposomes used for plasmid-mediated gene transfer strategies have various compositions, they are typically synthetic cationic lipids. Advantages of plasmid-liposome complexes include their ability to transfer large pieces of DNA encoding a therapeutic nucleic acid and their relatively low immunogenicity. Plasmids can be complexed with protein moieties to target specific cell surface receptors, if desired.

Plasmids are often used for short-term expression. However, a plasmid construct can be modified to obtain prolonged expression. It has recently been discovered that the inverted terminal repeats (ITR) of parvovirus, in particular adeno-associated virus (AAV), are responsible for the high-level persistent nucleic acid expression often associated with AAV (see, for example, U.S. Pat. No. 6,165,754). Accordingly, the expression vector can be a plasmid comprising native parvovirus ITRs to obtain prolonged and substantial expression of the therapeutic factor. While plasmids are suitable for use in the inventive method, preferably the expression vector is a viral vector.

AAV vectors are viral vectors of particular interest for use in gene therapy protocols. AAV is a DNA virus, which is not known to cause human disease. AAV requires co-infection with a helper virus (i.e., an adenovirus or a herpes virus), or expression of helper genes, for efficient replication. AAV vectors used for administration of a therapeutic nucleic acid have approximately 96% of the parental genome deleted, such that only the ITRs, which contain recognition signals for DNA replication and packaging, remain. This eliminates immunologic or toxic side effects due to expression of viral genes. In addition, delivering the AAV rep protein enables integration of the AAV vector comprising AAV ITRs into a specific region of genome, if desired. Host cells comprising an integrated AAV genome show no change in cell growth or morphology (see, for example, U.S. Pat. No. 4,797,368). Although efficient, the need for helper virus or helper genes can be an obstacle for widespread use of this vector.

Retrovirus is an RNA virus capable of infecting a wide variety of host cells. Upon infection, the retroviral genome integrates into the genome of its host cell and is replicated along with host cell DNA, thereby constantly producing viral RNA and any nucleic acid sequence incorporated into the retroviral genome. When employing pathogenic retroviruses, e.g., human immunodeficiency virus (HIV) or human T-cell lymphotrophic viruses (HTLV), care must be taken in altering the viral genome to eliminate toxicity. A retroviral vector can additionally be manipulated to render the virus replication-incompetent. As such, retroviral vectors are thought to be particularly useful for stable gene transfer in vivo. Lentiviral vectors, such as HIV-based vectors, are exemplary of retroviral vectors used for gene delivery.

HSV-based viral vectors are suitable for use as an expression vector to introduce nucleic acids into ocular cells. The mature HSV virion consists of an enveloped icosahedral capsid with a viral genome consisting of a linear double-stranded DNA molecule that is 152 kb. Most replication-deficient HSV vectors contain a deletion to remove one or more intermediate-early genes to prevent replication. The advantages of the herpes vector are its ability to enter a latent stage that can result in long-term DNA expression, and its large viral DNA genome that can accommodate exogenous DNA up to 25 kb. Of course, this ability is also a disadvantage in terms of short-term treatment regimens. For a description of HSV-based vectors appropriate for use in the inventive method, see, for example, U.S. Pat. Nos. 5,837,532; 5,846,782; 5,849,572; and 5,804,413 and International Patent Applications WO 91/02788, WO 96/04394, WO 98/15637, and WO 99/06583.

Adenovirus (Ad) is a 36 kb double-stranded DNA virus that efficiently transfers DNA in vivo to a variety of different target cell types. For use in the inventive method, the virus is preferably made replication deficient by deleting select genes required for viral replication. The expendable E3 region is also frequently deleted to allow additional room for a larger DNA insert. The vector can be produced in high titers and can efficiently transfer DNA to replicating and non-replicating cells. The newly transferred genetic information remains epichromosomal, thus eliminating the risks of random insertional mutagenesis and permanent alteration of the genotype of the target cell. However, if desired, the integrative properties of AAV can be conferred to adenovirus by constructing an AAV-Ad chimeric vector. For example, the AAV ITRs and nucleic acid encoding the Rep protein incorporated into an adenoviral vector enables the adenoviral vector to integrate into a mammalian cell genome. Therefore, AAV-Ad chimeric vectors are an interesting option for use in the invention. Similarly, conditionally replication-competent adenoviral vectors, wherein gene functions required for viral replication are encoded by the vector but expressed only in response to certain stimuli, can be used to deliver the nucleic acid sequence encoding the therapeutic factor to target cells. Such vectors are described in, for example, U.S. Pat. No. 5,998,205.

Preferably, the nucleic acid sequence encoding the therapeutic factor is incorporated into a viral vector; more preferably, the nucleic acid sequence encoding the therapeutic factor is present in an adenoviral vector. In the context of the invention, the adenoviral vector can be derived from, for example, any serotype of human adenovirus. Adenoviral stocks that can be employed as a source of adenovirus can be amplified from the adenoviral serotypes 1 through 51, which are currently available from the American Type Culture Collection (ATCC, Manassas, Va.), or from any other serotype of adenovirus available from any other source. For instance, an adenovirus can be of subgroup A (e.g., serotypes 12, 18, and 31), subgroup B (e.g., serotypes 3, 7, 11, 14, 16, 21, 34, and 35), subgroup C (e.g., serotypes 1, 2, 5, and 6), subgroup D (e.g., serotypes 8, 9, 10, 13, 15, 17, 19, 20, 22-30, 32, 33, 36-39, and 42-47), subgroup E (serotype 4), subgroup F (serotypes 40 and 41), or any other adenoviral serotype. Preferably, however, an adenovirus is of serotype 2, 5 or 9. However, non-group C adenoviruses can be used to prepare replication-deficient adenoviral gene transfer vectors for delivery of one or more therapeutic factors to ocular cells. Preferred adenoviruses used in the construction of non-group C adenoviral gene transfer vectors include Ad12 (group A), Ad7 (group B), Ad30 and Ad36 (group D), Ad4 (group E), and Ad41 (group F). Non-group C adenoviral vectors, methods of producing non-group C adenoviral vectors, and methods of using non-group C adenoviral vectors are disclosed in, for example, U.S. Pat. Nos. 5,801,030; 5,837,511; and 5,849,561 and International Patent Applications WO 97/12986 and WO 98/53087.

The adenoviral vector is preferably deficient in at least one replication-essential gene function (i.e., a gene function required for viral replication), thereby resulting in a "replication-deficient" adenoviral vector. Preferably, the adenoviral vector is deficient in at least one replication-essential gene function of the E1 region of the adenoviral genome (i.e., a gene function required for viral replication). In addition to a deficiency in the E1 region, the recombinant adenovirus can also have a mutation in the major late promoter (MLP). The mutation in the MLP can be in any of the MLP control elements such that it alters the responsiveness of the promoter, as discussed in International Patent Application WO 00/00628. More preferably, the vector is deficient in at least one replication-essential gene function of the E1 region and at least part of the E3 region (e.g., an Xba I deletion of the E3 region). With respect to the E1 region, the adenoviral vector can be deficient in at least part of the E1a region and/or at least part of the E1b region.

Preferably, the adenoviral vector is "multiply-deficient," meaning that the adenoviral vector is deficient in one or more replication-essential gene functions in each of two or more regions, i.e., the E1, E2, E4, L1, L2, L3, L4, and/or L5 regions. For example, the aforementioned E1-deficient or E1-, E3-deficient adenoviral vectors can be further deficient in at least one replication-essential gene function of the E4 region. Adenoviral vectors deleted of the entire E4 region can elicit lower host immune responses.

Alternatively, the adenoviral vector lacks all or part of the E1 region and all or part of the E2 region. However, adenoviral vectors lacking all or part of the E1 region, all or part of the E2 region, and all or part of the E3 region also are contemplated herein. In one embodiment, the adenoviral vector lacks all or part of the E1 region, all or part of the E2 region, all or part of the E3 region, and all or part of the E4 region. Suitable replication-deficient adenoviral vectors are disclosed in U.S.

Pat. Nos. 5,851,806 and 5,994,106 and International Patent Applications WO 95/34671 and WO 97/21826. For example, suitable replication-deficient adenoviral vectors include those with at least a partial deletion of the E1a region, at least a partial deletion of the E1b region, at least a partial deletion of the E2a region, and at least a partial deletion of the E3 region. Alternatively, the replication-deficient adenoviral vector can have at least a partial deletion of the E1 region, at least a partial deletion of the E3 region, and at least a partial deletion of the E4 region. Such multiply-deficient viral vectors are particularly useful in that such vectors can accept large inserts of exogenous DNA. Indeed, adenoviral amplicons, an example of a multiply-deficient adenoviral vector which comprises only those genomic sequences required for packaging and replication of the viral genome (e.g., at least one inverted terminal repeat (ITR) and packaging signal), can accept inserts of approximately 36 kb.

Therefore, in a preferred embodiment, the expression vector of the inventive method is a multiply-deficient adenoviral vector lacking all or part of the E1 region, all or part of the E3 region, all or part of the E4 region, and, optionally, all or part of the E2 region. In this regard, it has been observed that an at least E4-deficient adenoviral vector expresses a transgene at high levels for a limited amount of time in vivo and that persistence of expression of a transgene in an at least E4-deficient adenoviral vector can be modulated through the action of a trans-acting factor, such as HSV ICP0, Ad pTP, CMV-IE2, CMV-IE86, HIV tat, HTLV-tax, HBV-X, AAV Rep 78, the cellular factor from the U205 osteosarcoma cell line that functions like HSV ICP0, or the cellular factor in PC12 cells that is induced by nerve growth factor, among others. In view of the above, the multiply-deficient adenoviral vector (e.g., the at least E4-deficient adenoviral vector) preferably further comprises a nucleic acid sequence encoding a trans-acting factor that modulates the persistence of expression of the nucleic acid sequence encoding the therapeutic factor. Alternatively, a second nucleic acid sequence encoding a transacting factor that modulates the persistence of expression of the nucleic acid sequence encoding the therapeutic factor is administered to the eye. Preferably, the nucleic acid sequence encoding the trans-acting factor does not encode an adenoviral E4 region gene product. Whether expressed from the adenoviral vector or supplied by a second expression vector, preferably, the trans-acting factor is the *Herpes simplex* infected cell polypeptide 0 (HSV ICP0).

It should be appreciated that the deletion of different regions of a viral vector can alter the immune response of the mammal. For example, deletion of different regions can reduce the inflammatory response generated by the adenoviral vector. Furthermore, the adenoviral vector's coat protein can be modified so as to decrease the adenoviral vector's ability or inability to be recognized by a neutralizing antibody directed against the wild-type coat protein, as described in International Patent Application WO 98/40509. Such modifications are useful for long-term treatment of persistent ocular neovascularization.

Similarly, the coat protein of a viral vector, preferably an adenoviral vector, can be manipulated to alter the binding specificity or recognition of a virus for a viral receptor on a potential host cell. For adenovirus, such manipulations can include deletion of regions of the fiber, penton, hexon, pIIa, pVI, and pIX, insertions of various native or normative ligands into portions of the coat protein, and the like. Manipulation of the coat protein can broaden the range of cells infected by a viral vector or enable targeting of a viral vector to a specific cell type. For example, in one embodiment, the expression vector is a viral vector comprising a chimeric coat protein (e.g., a fiber, hexon, pIX, pIIIa, or penton protein), which differs from the wild-type (i.e., native) coat protein by the introduction of a normative amino acid sequence, preferably at or near the carboxyl terminus. Preferably, the normative amino acid sequence is inserted into or in place of a coat protein sequence. The normative amino acid sequence can be inserted within the internal coat protein sequence or at the end of the coat protein sequence. The resultant chimeric viral coat protein is able to direct entry into cells of the viral, i.e., adenoviral, vector comprising the coat protein that is more efficient than entry into cells of a vector that is identical except for comprising a wild-type viral coat protein rather than the chimeric viral coat protein. Preferably, the chimeric virus coat protein binds a novel endogenous binding site present on the cell surface that is not recognized, or is poorly recognized by a vector comprising a wild-type coat protein. One direct result of this increased efficiency of entry is that the virus, preferably, the adenovirus, can bind to and enter cell types which a virus comprising wild-type coat protein typically cannot enter or can enter with only a low efficiency.

In another embodiment of the invention, the nucleic acid sequence is present in a viral vector comprising a chimeric virus coat protein not selective for a specific type of eukaryotic cell. The chimeric coat protein differs from the wild-type coat protein by an insertion of a normative amino acid sequence into or in place of an internal coat protein sequence. In this embodiment, the chimeric virus coat protein efficiently binds to a broader range of eukaryotic cells than a wild-type virus coat, such as described in International Patent Application WO 97/20051.

Specificity of binding of an adenovirus to a given cell can also be adjusted by use of an adenovirus comprising a short-shafted adenoviral fiber gene, as discussed in U.S. Pat. No. 5,962,311. Use of an adenovirus comprising a short-shafted adenoviral fiber gene reduces the level or efficiency of adenoviral fiber binding to its cell-surface receptor and increases adenoviral penton base binding to its cell-surface receptor, thereby increasing the specificity of binding of the adenovirus to a given cell. Alternatively, use of an adenovirus comprising a short-shafted fiber enables targeting of the adenovirus to a desired cell-surface receptor by the introduction of a normative amino acid sequence either into the penton base or the fiber knob.

In addition, the coat protein of a viral vector, in particular an adenoviral vector, can be manipulated to ablate native binding of the coat protein to cell surface receptors. Ablation of native binding of the adenoviral coat proteins, e.g., ablation of those amino acid sequences in the fiber and penton associated with binding to the coxsackie and adenovirus receptor (CAR) and integrins, respectively, can be advantageous in generating targeted vectors.

Of course, the ability of a viral vector to recognize a potential host cell can be modulated without genetic manipulation of the coat protein. For instance, complexing an adenovirus with a bispecific molecule comprising a penton base-binding domain and a domain that selectively binds a particular cell surface binding site enables one of ordinary skill in the art to target the vector to a particular cell type.

Suitable modifications to a viral vector, specifically an adenoviral vector, are described in U.S. Pat. Nos. 5,559,099; 5,731,190; 5,712,136; 5,770,442; 5,846,782; 5,926,311; 5,965,541; 6,057,155; 6,127,525; 6,153,435; 6,329,190; and 6,455,314 and International Patent Applications WO 96/07734, WO 96/26281, WO 97/20051, WO 98/07865, WO 98/07877, WO 98/54346, WO 00/15823, WO 01/58940, and WO 01/92549. Similarly, it will be appreciated that numerous expression vectors are available commercially. Construction of expression vectors is well understood in the art. Adenoviral vectors can be constructed and/or purified using the methods set forth, for example, in U.S. Pat. No. 5,965,358 and International Patent Applications WO 98/56937, WO 99/15686, and WO 99/54441. Adeno-associated viral vectors can be constructed and/or purified using the methods set forth, for example, in U.S. Pat. No. 4,797,368 and Laughlin et al., *Gene*, 23, 65-73 (1983).

The selection of an expression (i.e., delivery) vector for use in the inventive method to administer the nucleic acid sequence encoding the therapeutic factor will depend on a variety of factors such as, for instance, the host, immunogenicity of the vector, the desired duration of protein production, and the like. As each type of expression vector has distinct properties, a researcher has the freedom to tailor the inventive method to any particular situation. Moreover, more than one type of expression vector (i.e., a plasmid and a viral vector or two different viral vectors) can be used to deliver the nucleic acid sequence to the ocular cell. Thus, the invention can comprise directly administering to the eye, thereby contacting an ocular cell, with different expression vectors, each comprising the nucleic acid sequence encoding the therapeutic factor. The nucleic acid sequence encoding the therapeutic factor is expressed, thereby resulting in the production of the therapeutic factor to prophylactically or therapeutically treat ocular neovascularization in an animal. If multiple types of expression vectors are used, preferably an adenoviral vector and an adeno-associated viral vector are directly administered to the eye. One of ordinary skill in the art will appreciate the ability to capitalize on the advantageous properties of multiple delivery systems to treat or study ocular neovascularization.

The nucleic acid sequence encoding the therapeutic factor is desirably operably linked to regulatory sequences necessary for expression, e.g., a promoter. A "promoter" is a DNA sequence that directs the binding of RNA polymerase and thereby promotes RNA synthesis. A nucleic acid sequence is "operably linked" to a promoter when the promoter is capable of directing transcription of that nucleic acid sequence. A promoter can be native or normative to the nucleic acid sequence to which it is operably linked.

Any promoter (i.e., whether isolated from nature or produced by recombinant DNA or synthetic techniques) can be used in connection with the invention to provide for transcription of the nucleic acid sequence. The promoter preferably is capable of directing transcription in a eukaryotic (desirably mammalian) cell. The functioning of the promoter can be altered by the presence of one or more enhancers and/or silencers present on the vector. "Enhancers" are cis-acting elements of DNA that stimulate or inhibit transcription of adjacent genes. An enhancer that inhibits transcription also is termed a "silencer." Enhancers differ from DNA-binding sites for sequence-specific DNA binding proteins found only in the promoter (which also are termed "promoter elements") in that enhancers can function in either orientation, and over distances of up to several kilobase pairs (kb), even from a position downstream of a transcribed region.

A comparison of promoter sequences that function in eukaryotes has revealed conserved sequence elements. Generally, eukaryotic promoters transcribed by RNA polymerase II are typified by a "TATA box" centered at approximately position −25, which appears to be essential for accurately positioning the start of transcription. The TATA box directs RNA polymerase to begin transcribing approximately 30 base pairs (bp) downstream in mammalian systems. The TATA box functions in conjunction with at least two other upstream sequences located about 40 bp and 110 bp upstream of the start of transcription. Typically, a so-called "CCAAT box" serves as one of the two upstream sequences, and the other often is a GC-rich segment. The CCAAT homology can reside on different strands of the DNA. The upstream promoter element also can be a specialized signal such as one of those which have been described in the art and which appear to characterize a certain subset of genes.

To initiate transcription, the TATA box and the upstream sequences are each recognized by regulatory proteins which bind to these sites, and activate transcription by enabling RNA polymerase II to bind the DNA segment and properly initiate transcription. Whereas base changes outside the TATA box and the upstream sequences have little effect on levels of transcription, base changes in either of these elements substantially lower transcription rates (see, e.g., Myers et al., *Science*, 229, 242-247 (1985); McKnight et al., *Science*, 217, 316-324 (1982)). The position and orientation of these elements relative to one another, and to the start site, are important for the efficient transcription of some, but not all, coding sequences. For instance, some promoters function well in the absence of any TATA box. Similarly, the necessity of these and other sequences for promoters recognized by RNA polymerase I or III, or other RNA polymerases, can differ.

Accordingly, promoter regions can vary in length and sequence and can further encompass one or more DNA binding sites for sequence-specific DNA binding proteins and/or an enhancer or silencer. Enhancers and/or silencers can similarly be present on a nucleic acid sequence outside of the promoter per se.

The invention preferentially employs a viral promoter. Suitable viral promoters are known in the art and include, for instance, cytomegalovirus (CMV) promoters, such as the CMV immediate-early promoter, promoters derived from human immunodeficiency virus (HIV), such as the HIV long terminal repeat promoter, Rous sarcoma virus (RSV) promoters, such as the RSV long terminal repeat, mouse mammary tumor virus (MMTV) promoters, HSV promoters, such as the Lap2 promoter or the herpes thymidine kinase promoter (Wagner et al., *Proc. Natl. Acad. Sci.*, 78, 144-145 (1981)), promoters derived from SV40 or Epstein Barr virus, adeno-associated viral promoters, such as the p5 promoter, and the like. Preferably, the viral promoter is an adenoviral promoter, such as the Ad2 or Ad5 major late promoter and tripartite leader, a CMV promoter, or an RSV promoter.

Many of the above-described promoters are constitutive promoters. Instead of being a constitutive promoter, the promoter can be an inducible promoter, i.e., a promoter that is up- and/or down-regulated in response to appropriate signals. For instance, the regulatory sequences can comprise a hypoxia driven promoter, which is active when the ocular neovascularization is associated with hypoxia. Other examples of suitable inducible promoter systems include, but are not limited to, the IL-8 promoter, the metallothionine inducible promoter system, the bacterial lacZYA expression system, the tetracycline expression system, and the T7 polymerase system. Further, promoters that are selectively activated at different developmental stages (e.g., globin genes are differentially transcribed from globin-associated promoters in embryos and adults) can be employed. The promoter sequence that regulates expression of the nucleic acid sequence can contain at least one heterologous regulatory sequence responsive to regulation by an exogenous agent. The regulatory sequences are preferably responsive to an exogenous agent such as, but not limited to, a drug, a hormone, or another gene product. For example, the regulatory sequence, e.g., promoter, preferably is responsive to a glucocorticoid receptor-hormone complex, which, in turn, enhances the level of transcription of a therapeutic peptide or a therapeutic fragment thereof.

Preferably, the regulatory sequence comprises a tissue-specific promoter, i.e., a promoter that is preferentially activated in a given tissue and results in expression of a gene product in the tissue where activated. A typically used tissue-specific promoter is a myocyte-specific promoter. A tissue specific promoter for use in the inventive vector can be chosen by the ordinarily skilled artisan based upon the target tissue or cell-type. Preferred tissue-specific promoters for use in the inventive methods are specific to ocular tissue, such as a rhodopsin promoter. Examples of rhodopsin promoters include, but are not limited to, a GNAT cone-transducing alpha-subunit gene promoter or an interphotoreceptor retinoid binding protein promoter.

One of ordinary skill in the art will appreciate that each promoter drives transcription, and, therefore, protein expression, differently with respect to time and the amount of protein produced. For example, the CMV promoter is characterized as having peak activity shortly after transduction, i.e., about 24 hours after transduction, then quickly tapering off. On the other hand, the RSV promoter's activity increases gradually, reaching peak activity several days after transduction, and maintains a high level of activity for several weeks. Indeed, sustained expression driven by an RSV promoter has been observed in all cell types studied, including, for instance, liver cells, lung cells, spleen cells, diaphragm cells, skeletal muscle cells, and cardiac muscle cells. Thus, a promoter can be selected for use in the method of the invention by matching its particular pattern of activity with the desired pattern and level of expression of at least one inhibitor of angiogenesis and/or at least one neurotrophic factor. Alternatively, a hybrid promoter can be constructed which combines the desirable aspects of multiple promoters. For example, a CMV-RSV hybrid promoter combining the CMV promoter's initial rush of activity with the RSV promoter's high maintenance level of activity would be especially preferred for use in many embodiments of the inventive method. It is also possible to select a promoter with an expression profile that can be manipulated by an investigator.

Also preferably, the expression vector comprises a nucleic acid encoding a cis-acting factor, wherein the cis-acting factor modulates the expression of the nucleic acid sequence. Preferably, the cis-acting factor comprises matrix attachment region (MAR) sequences (e.g., immunoglobulin heavy chain (Jenunwin et al., *Nature,* 385(16), 269 (1997)), apolipoprotein B, or locus control region (LCR) sequences, among others. MAR sequences have been characterized as DNA sequences that associate with the nuclear matrix after a combination of nuclease digestion and extraction (Bode et al., *Science,* 255(5041), 195-197 (1992)). MAR sequences are often associated with enhancer-type regulatory regions and, when integrated into genomic DNA, MAR sequences augment transcriptional activity of adjacent nucleotide sequences. It has been postulated that MAR sequences play a role in controlling the topological state of chromatin structures, thereby facilitating the formation of transcriptionally-active complexes. Similarly, it is believed LCR sequences function to establish and/or maintain domains permissive for transcription. Many LCR sequences give tissue specific expression of associated nucleic acid sequences. Addition of MAR or LCR sequences to the expression vector can further enhance expression of at least one inhibitor of angiogenesis and/or at least one neurotrophic factor.

With respect to promoters, nucleic acid sequences, selectable markers, and the like, located on an expression vector comprising the nucleic acid sequence encoding the therapeutic factor according to the invention, such elements can be present as part of a cassette, either independently or coupled. In the context of the invention, a "cassette" is a particular base sequence that possesses functions which facilitate subcloning and recovery of nucleic acid sequences (e.g., one or more restriction sites) or expression (e.g., polyadenylation or splice sites) of particular nucleic acid sequences.

The construction of an exogenous nucleic acid operably linked to regulatory sequences necessary for expression is well within the skill of the art (see, for example, Sambrook et al., *Molecular Cloning: A Laboratory Manual,* 2d ed. (1989)). With respect to the expression of the nucleic acid sequence encoding the therapeutic factor (as well as other nucleic acid sequences) according to the invention, the ordinary skilled artisan is aware that different genetic signals and processing events control levels of nucleic acids and proteins/peptides in a cell, such as, for example, transcription, mRNA translation, and post-transcriptional processing. The transcription of DNA into RNA requires a functional promoter, as described herein.

Protein expression is dependent on the level of RNA transcription that is regulated by DNA signals, and the levels of DNA template. Similarly, translation of mRNA requires, at the very least, an AUG initiation codon, which is usually located within 10 to 100 nucleotides of the 5' end of the message. Sequences flanking the AUG initiator codon have been shown to influence its recognition by eulcaryotic ribosomes, with conformity to a perfect Kozak consensus sequence resulting in optimal translation (see, e.g., Kozak, *J. Molec. Biol.,* 196, 947-950 (1987)). Also, successful expression of an exogenous nucleic acid in a cell can require post-translational modification of a resultant protein. Thus, production of a protein can be affected by the efficiency with which DNA (or RNA) is transcribed into mRNA, the efficiency with which mRNA is translated into protein, and the ability of the cell to carry out post-translational modification. These are all factors of which the ordinary skilled artisan is aware and is capable of manipulating using standard means to achieve the desired end result.

Along these lines, to optimize protein production, preferably the nucleic acid sequence further comprises a polyadenylation site following the coding region of the nucleic acid sequence. Also, preferably all the proper transcription signals (and translation signals, where appropriate) are correctly arranged such that the nucleic acid sequence will be properly expressed in the cells into which it is introduced. If desired, the nucleic acid sequence also can incorporate splice sites (i.e., splice acceptor and splice donor sites) to facilitate mRNA production. Moreover, if the nucleic acid sequence encodes a protein or peptide, which is a processed or secreted protein or acts intracellularly, preferably the nucleic acid sequence further comprises the appropriate sequences for processing, secretion, intracellular localization, and the like.

In certain embodiments, it may be advantageous to modulate production of the therapeutic factor. An especially preferred method of modulating expression of a nucleic acid sequence comprises addition of site-specific recombination sites on the expression vector. Contacting a nucleic acid sequence comprising site-specific recombination sites with a recombinase will either up- or down-regulate transcription of a coding sequence, or simultaneously up-regulate transcription of one coding sequence and down-regulate transcription of another, through the recombination event. Use of site-specific recombination to modulate transcription of a nucleic acid sequence is described in, for example, U.S. Pat. Nos. 5,801,030 and 6,063,627 and International Patent Application WO 97/09439.

Preferably, the therapeutic factor that selectively promotes apoptosis of endothelial cells associated with neovascularization is an inhibitor of angiogenesis, e.g., the therapeutic factor induces apoptosis in cells associated with neovascularization. When a nucleic acid sequence is administered, the nucleic acid sequence preferably encodes an inhibitor of angiogenesis that induces apoptosis of endothelial cells associated with neovascularization to a greater degree than endothelial cells associated with existing vasculature. Multiple therapeutic factors, e.g., inhibitors of angiogenesis, can be administered to the eye. By "inhibitor of angiogenesis" is meant any factor that prevents or ameliorates neovascularization. Examples of suitable inhibitors of angiogenesis that selectively induce apoptosis of endothelial cells associated with neovascularization include, but are not limited to, PEDF and endostatin. One of ordinary skill in the art will understand that complete prevention or amelioration of neovascularization is not required in order to realize a therapeutic effect. Therefore, the inventive method contemplates both partial and complete prevention and amelioration of angiogenesis. One of ordinary skill in the art will appreciate that the therapeutic factor can be modified or truncated and retain activity.

Endostatin is a carboxy-terminal peptide of collagen XVIII. The anti-angiogenic peptide has been demonstrated to inhibit endothelial cell proliferation, induce apoptosis of endothelial cells in vitro (Dhanabal et al., *J. Biol. Chem.*, 274(17), 11721-11726 (1999)), and reduce tumor size in mice (Chen et al., *Human Gene Therapy*, 11, 1983-1996 (2000)). The endostatin protein is relatively nontoxic, and biologically-relevant amounts of the protein have been produced in vivo using a variety of gene transfer vectors.

The therapeutic factor that selectively induces apoptosis in endothelial cells associated with neovascularization also can have neurotrophic activity (e.g., neurotrophic factor or neurotrophic agent). Neurotrophic factors are thought to be responsible for the maturation of developing neurons and for maintaining adult neurons and, therefore, are useful for maintaining the viability or prolonging survival of photoreceptor cells. Neurotrophic factors are divided into three subclasses: neuropoietic cytokines; neurotrophins; and fibroblast growth factors. Ciliary neurotrophic factor (CNTF) is exemplary of neuropoietic cytokines. CNTF promotes the survival of ciliary ganglionic neurons and supports certain neurons that are NGF-responsive. Neurotrophins include, for example, brain-derived neurotrophic factor and nerve growth factor, perhaps the best characterized neurotrophic factor. Other neurotrophic factors suitable for being encoded by the nucleic acid sequence of the inventive method includes, for example, transforming growth factors, glial cell-line derived neurotrophic factor, neurotrophin 3, neurotrophin 4/5, and interleukin 1-$\beta$. Neurotrophic factors associated with angiogenesis, such as aFGF and bFGF, are less preferred. The neurotrophic factor of the inventive method also can be a neuronotrophic factor, e.g., a factor that enhances neuronal survival. It has been postulated that neurotrophic factors can actually reverse degradation of neurons. Such factors, conceivably, are useful in treating the degeneration of neurons associated with vision loss and caused by neovascularization. Neurotrophic factors function in both paracrine and autocrine fashions, making them ideal therapeutic agents. Preferably, the therapeutic factor comprises both anti-angiogenic activity and neurotrophic activity. Most preferably, the therapeutic factor is pigment epithelium-derived factor (PEDF).

PEDF, also named early population doubling factor-1 (EPC-1), is a secreted protein having homology to a family of serine protease inhibitors named serpins. PEDF is made predominantly by retinal pigment epithelial cells and is detectable in most tissues and cell types of the body. PEDF has been observed to induce differentiation in retinoblastoma cells and enhance survival of neuronal populations (Chader, *Cell Different.*, 20, 209-216 (1987)). Factors that enhance neuronal survival under adverse conditions, such as PEDF, are termed "neuronotrophic," as described herein. PEDF further has gliastatic activity, i.e., the ability to inhibit glial cell growth. As discussed above, PEDF also has anti-angiogenic activity. Anti-angiogenic derivatives of PEDF include SLED proteins, discussed in International Patent Application WO 99/04806. It has also been postulated that PEDF is involved with cell senescence (Pignolo et al., *J. Biol. Chem.*, 268(12), 8949-8957 (1998)). PEDF for use in the inventive method can be derived from any source, and is further characterized in U.S. Pat. No. 5,840,686 and International Patent Applications WO 93/24529 and WO 99/04806.

The therapeutic factor or the nucleic acid sequence encoding the therapeutic factor, e.g., PEDF, can be obtained from any source, e.g., isolated from nature, synthetically or recombinantly generated, isolated from a genetically engineered organism, and the like. In nature, PEDF is almost solely generated in human fetus retinal cells. The poor production of human PEDF from RPE cells and the scarcity of source tissue of PEDF complicates the use of this potentially valuable therapeutic factor. A viral vector comprising the nucleic acid sequence encoding PEDF can be used to create sufficient amounts of recombinant PEDF protein in cell culture, or can be directly administered to the eye to produce recombinant PEDF protein intraocularly or extraocularly (e.g., to produce recombinant PEDF in the ocular orbit or cells of the ocular apparatus).

Active fragments of the therapeutic factor (i.e., those fragments having biological activity sufficient to induce apoptosis of endothelial cells associated with neovascularization) are suitable for use in the inventive method. Likewise, a fusion protein comprising the therapeutic factor or a therapeutic fragment thereof and for example, a moiety that stabilizes peptide conformation, also can be used. The ordinarily skilled artisan has the ability to determine whether a modified therapeutic factor or a fragment thereof has the ability to selectively induce apoptosis in endothelial cells associated with neovascularization using, for example, the TdT-dUTP terminal nick end-labeling (TUNEL) assay in conjunction with models of angiogenesis, such as in vitro angiogenesis assays, (e.g., Matrigel-based assays), the mouse ear model of neovascularization, and the rat hindlimb ischemia model. Ideally, the angiogenesis model will involve neovascularization of the eye, such as transgenic mice comprising an exogenous VEGF gene operably linked to the rhodopsin promoter, which provides an ocular angiogenesis model in which neovascularization sprouts from the retinal capillary bed and invades the photoreceptor layer and subretinal space (see, for example, Okamato et al., *Am. J. Pathol.*, 151, 281-291 (1997), or To be et al., *Invest. Opthalmol. Vis. Sci.*, 39, 180-188 (1998)). Alternatively, disruption of Bruch's membrane in the eyes of mice or rabbits provides a reliable model of CNV (see, for example, To be et al., *Am. J. Pathol.*, 153, 1641-1646 (1998)).

The invention also contemplates the use of nucleic acid sequences encoding chimeric or fusion peptides in the inventive method. Through recombinant DNA technology, scientists have been able to generate fusion proteins that contain the combined amino acid sequence of two or more proteins. The ordinarily skilled artisan can fuse the active domains of two or more factors to generate chimeric peptides with desired activity. The chimeric peptide can comprise the entire amino acid sequences of two or more peptides or, alternatively, can be constructed to comprise portions of two or more peptides (e.g., 10, 20, 50, 75, 100, 400, 500, or more amino acid residues). Desirably, the chimeric peptide comprises anti-angiogenic and neurotrophic activity, which can be determined using routine methods.

Additional agents can be administered in conjunction with the therapeutic factor or nucleic acid sequence encoding the therapeutic factor. For example, additional therapeutic peptides, such as anti-inflammatory peptides, immune suppressors, anti-angiogenic factors, or neurotrophic factors, are administered before, during, or after administration of the therapeutic factor that selectively induces apoptosis in endothelial cells associated with neovascularization.

The method of the invention can be part of a treatment regimen involving other therapeutic modalities. Accordingly, the ocular neovascularization, e.g., choroidal neovascularization or retinal neovascularization, can be treated in accordance with the inventive method prior to, during, or after treatment with any of a number of ocular therapies, such as drug therapy, photodynamic therapy, photocoagulation laser therapy, panretinal therapy, thermotherapy, radiation therapy, or surgery. Preferably, the surgery is removal of subretinal blood or removal of subretinal choroidal neovascular membrane. For example, the nucleic acid sequence encoding the therapeutic factor (or the therapeutic factor itself) can be administered intraocularly or periocularly (e.g., sub-tenon delivery) for the prophylactic or therapeutic treatment of persistent or recurrent ocular neovascularization treated with surgery, laser photocoagulation, and photodynamic therapies.

The therapeutic factor or nucleic acid sequence encoding the therapeutic factor is preferably administered as soon as possible after it has been determined that an animal, such as a mammal, specifically a human, is at risk for ocular neovascularization (prophylactic treatment) or has begun to develop ocular neovascularization (therapeutic treatment). Treatment will depend, in part, upon the particular therapeutic factor used, the particular nucleic acid sequence used (if appropriate), the route of administration, and the cause and extent, if any, of ocular neovascularization realized. For example, systemic administration or administration to both eyes is preferred in the prophylactic treatment of neovascularization associated with macular degeneration because, once one eye is affected, the other eye is at risk (up to 19% per year).

The therapeutic factor or nucleic acid sequence encoding the therapeutic factor desirably is administered in a pharmaceutical composition (e.g., a pharmaceutical composition comprising a pharmaceutically acceptable carrier and the nucleic acid sequence encoding the therapeutic factor). Any suitable pharmaceutically acceptable carrier (e.g., pharmacologically or physiologically acceptable carrier) can be used within the context of the invention, and such carriers are well known in the art. The choice of carrier will be determined, in part, by the particular site to which the composition is to be administered and the particular method used to administer the composition.

Suitable formulations include aqueous and non-aqueous solutions, isotonic sterile solutions, which can contain antioxidants, buffers, bacteriostats, and solutes that render the formulation isotonic with the blood or intraocular fluid of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets of the kind previously described. When administering a nucleic acid sequence or peptide, preferably the pharmaceutically acceptable carrier is a buffered saline solution. More preferably, the nucleic acid sequence or peptide is administered in a pharmaceutical composition formulated to protect the nucleic acid or peptide sequence from damage prior to administration. For example, the pharmaceutical composition can be formulated to reduce loss of the nucleic acid sequence or peptide on devices used to prepare, store, or administer the nucleic acid sequence or therapeutic factor, such as glassware, syringes, or needles. The pharmaceutical composition can be formulated to decrease the light sensitivity and/or temperature sensitivity of the nucleic acid sequence or the therapeutic factor itself. To this end, the pharmaceutical composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. The use of such a pharmaceutical composition will extend the shelf life of the therapeutic factor or nucleic acid sequence encoding the therapeutic factor, facilitate administration, and increase the efficiency of the inventive method. In this regard, a pharmaceutical composition also can be formulated to enhance transduction efficiency. See, for example, U.S. Pat. No. 6,225,289 and International Patent Application WO 00/34444 for a discussion of formulations suitable for pharmaceutical compositions.

In addition, one of ordinary skill in the art will appreciate that the therapeutic factor or the nucleic acid sequence encoding the therapeutic factor, e.g., a viral vector comprising the nucleic acid sequence, can be present in a composition with other therapeutic or biologically-active agents. For example, therapeutic factors useful in the treatment of a particular indication can be present. For instance, if treating vision loss, hyaluronidase can be added to a composition to affect the break down of blood and blood proteins in the vitreous of the eye. Factors that control inflammation, such as ibuprofen or steroids, can be part of the composition to reduce swelling and inflammation associated with in vivo administration of the viral vector and ocular distress. Immune system suppressors can be administered in combination with the inventive method to reduce any immune response to the vector itself or associated with an ocular disorder. Anti-angiogenic factors, such as soluble growth factor receptors, growth factor antagonists, i.e., angiotensin, and the like also can be part of the composition, as well as additional neurotrophic factors. Similarly, vitamins and minerals, anti-oxidants, and micronutrients can be co-administered. Antibiotics, i.e., microbicides and fungicides, can be present to reduce the risk of infection associated with gene transfer procedures and other disorders.

Suitable methods, i.e., invasive and noninvasive methods, of directly administering a therapeutic factor or a nucleic acid sequence encoding a therapeutic factor, whereon the therapeutic factor or nucleic acid sequence will contact an ocular cell, are available. By "direct administration" is meant introduction of the therapeutic factor or nucleic acid sequence encoding the therapeutic factor to the eye. Although more than one route can be used for direct administration, a particular route can provide a more immediate and more effective reaction than another route. Accordingly, the described routes of administration are merely exemplary and are in no way limiting.

The inventive method is not dependent on the mode of administering the therapeutic factor or nucleic acid sequence encoding the therapeutic factor to an animal, preferably a human, to achieve the desired effect. As such, any route of administration is appropriate so long as the therapeutic factor is administered directly to the eye and contacts an endothelial cell associated with neovascularization. The therapeutic factor or nucleic acid sequence encoding the therapeutic factor can be appropriately formulated and administered in the form of an injection, eye lotion, ointment, implant and the like. For instance, an expression vector comprising the nucleic acid sequence of the inventive method can be applied, for example, topically, subconjunctivally, intraocularly, retrobulbarly, periocularly (e.g., via sub-tenon injection), subretinally, or suprachoroidally. In certain cases, it may be appropriate to administer multiple applications and employ multiple routes, e.g., subretinal and intravitreous, to ensure sufficient exposure of ocular cells to the therapeutic factor or nucleic acid sequence encoding the therapeutic factor to achieve the desired effect.

Depending on the particular case, it may be desirable to non-invasively administer the therapeutic factor or nucleic acid sequence encoding the therapeutic factor to a patient. For instance, if multiple surgeries have been performed, the patient displays low tolerance to anesthetic, or if other ocular-related disorders exist, topical administration of the therapeutic factor or nucleic acid sequence encoding the therapeutic factor may be most appropriate. Topical formulations are well known to those of skill in the art. The use of patches, corneal shields (see, e.g., U.S. Pat. No. 5,185,152), and ophthalmic solutions (see, e.g., U.S. Pat. No. 5,710,182) and ointments, e.g., eye drops, is also within the skill in the art. If desired, the therapeutic factor or the nucleic acid sequence encoding the therapeutic factor can be administered non-invasively using a needleless injection device, such as the Biojector 2000 Needle-Free Injection Management System® available from Bioject, Inc.

The therapeutic factor or nucleic acid sequence encoding the therapeutic factor is preferably present in or on a device that allows controlled or sustained release, such as an ocular sponge, meshwork, mechanical reservoir, or mechanical implant. Implants (see, e.g., U.S. Pat. Nos. 4,853,224, 4,997,652, and 5,443,505), devices (see, e.g., U.S. Pat. Nos. 4,863,457, 5,098,443, 5,554,187, and 5,725,493), such as an implantable device, e.g., a mechanical reservoir, an intraocular device, or an extraocular device with an intraocular conduit, especially an implant or a device comprised of a polymeric composition, are particularly useful for ocular administration of the therapeutic factor or nucleic acid sequence encoding the therapeutic factor. The therapeutic factor or nucleic acid sequence encoding the therapeutic factor also can be administered in the form of a sustained-release formulation (see, e.g., U.S. Pat. No. 5,378,475) comprising, for example, gelatin, chondroitin sulfate, a polyphosphoester, such as bis-2-hydroxyethyl-terephthalate (BHET), or a polylactic-glycolic acid.

Alternatively, the therapeutic factor or nucleic acid sequence encoding the therapeutic factor can be administered using invasive procedures, such as, for instance, intravitreal injection or subretinal injection, optionally preceded by a vitrectomy. Subretinal injections can be administered to different compartments of the eye, e.g., the anterior chamber or posterior chamber. Pharmaceutically acceptable carriers for injectable compositions are well-known to those of ordinary skill in the art (see *Pharmaceutics and Pharmacy Practice*, J.B. Lippincott Co., Philadelphia, Pa., Banker and Chalmers, eds., pages 238-250 (1982), and *ASHP Handbook on Injectable Drugs*, Toissel, 4$^{th}$ ed., pages 622-630 (1986)).

In some embodiments, it is advantageous to deliver the therapeutic factor or nucleic acid encoding the therapeutic factor via periocular (e.g., episcleral, sub-tenon, or sub-conjunctival) injection. For example, most standard injection techniques require puncturing layers of the eye, including the sclera, choroid, retina, etc. To minimize trauma to those layers of the eye, the therapeutic factor or nucleic acid encoding the therapeutic factor can be administered into the sub-tenon (i.e., episcleral) space surrounding the scleral portion of the eye. The sub-tenon space is enclosed by Tenon's capsule, a fibrous sheath encasing the posterior segment of the eye. Puncture of this fibrous sheath with an injection device is less traumatic to the layers of the eye responsible for vision. In addition, when the nucleic acid sequence encoding the therapeutic factor is present in a viral vector, vector-related toxicity to intraocular cells is minimized, as at least a portion of the dose of vector transduces cells of the sub-tenon space, where the nucleic acid sequence encoding therapeutic factor is expressed and the therapeutic factor thereby produced is transported to intraocular cells. Due to the structure of Tenon's capsule, the exposure of non-ocular cells to the therapeutic factor or nucleic acid sequence encoding the therapeutic factor is limited. Sub-tenon injection also allows the administration of a greater volume of therapeutic composition compared to that allowed by, for example, subretinal injection.

In most cases, sub-tenon delivery of a composition to the eye involves surgically opening Tenon's capsule and injecting into the sub-tenon space using a syringe or cannula. Alternatively, Tenon's capsule is grasped by the practitioner, not surgically opened, and the therapeutic composition is injected into the sub-tenon space using, for example, a syringe. The therapeutic factor or nucleic acid encoding the therapeutic factor can be administered to other regions of the ocular apparatus such as, for instance, the ocular muscles, the orbital fascia, the eye lid, the lacrimal apparatus, and the like as is appropriate.

Preferably, the therapeutic factor or nucleic acid sequence encoding the therapeutic factor is administered via an ophthalmologic instrument for delivery to a specific region of an eye, e.g., the sub-tenon space. The use of a specialized ophthalmologic instrument ensures precise administration of the therapeutic factor or the nucleic acid sequence encoding the therapeutic factor, while minimizing damage to adjacent ocular tissue. Delivery of the therapeutic factor or nucleic acid sequence encoding the therapeutic factor to a specific region of the eye also limits exposure of unaffected cells to the therapeutic factor, thereby reducing the risk of side effects. A preferred ophthalmologic instrument is a combination of forceps and subretinal needle or sharp bent cannula.

When administering the therapeutic factor or the nucleic acid sequence encoding the therapeutic factor, appropriate dosage and route of administration can be selected to minimize loss of the therapeutic factor or nucleic acid sequence or inactivation of the therapeutic factor due to a host's immune system. For example, for contacting ocular cells in vivo, it can be advantageous to administer to a host a null expression vector (i.e., an expression vector not comprising the nucleic acid sequence encoding the therapeutic factor) prior to performing the inventive method. Prior administration of a null expression vector can serve to create immunity in the host to the expression vector, thereby decreasing the amount of therapeutic vector cleared by the immune system. The therapeutic factor, itself, can be manipulated to mask immunogenic epitopes or co-administered with an immunosuppressant.

The dose of therapeutic factor or nucleic acid sequence encoding the therapeutic factor administered to an animal, particularly a human, in accordance with the invention should be sufficient to effect the desired response (selective induction of apoptosis in endothelial cells associated with neovascularization in the animal over a reasonable time frame). Dosage will depend upon a variety of factors, including the age, species, the pathology in question, and condition or disease state. Dosage also depends on the therapeutic factor, as well as the amount of ocular tissue about to be affected or actually affected by the ocular-related disease. The size of the dose also will be determined by the route, timing, and frequency of administration as well as the existence, nature, and extent of any adverse side effects that might accompany the administration of a particular therapeutic factor or nucleic acid sequence encoding the therapeutic factor, and the desired physiological effect. It will be appreciated by one of ordinary skill in the art that various conditions or disease states, in particular, chronic conditions or disease states, may require prolonged treatment involving multiple administrations.

Suitable doses and dosage regimens can be determined by conventional range-finding techniques known to those of ordinary skill in the art. When administering a peptide, preferably from about 0.5 mg to about 6 mg of therapeutic factor, more preferably about 2 mg to about 6 mg of therapeutic factor, is administered per eye. More preferably, from about 3 mg to about 5 mg peptide is administered per eye. Most preferably, 4 mg peptide is administered per eye. When using a viral vector, preferably about $10^6$ viral particles to about $10^{12}$ viral particles are delivered to the eye. In other words, a pharmaceutical composition can be administered that comprises a viral vector concentration of from about $10^6$ particles/ml to about $10^{12}$ particles/ml (including all integers within the range of about $10^6$ particles/ml to about $10^{12}$ particles/ml, e.g., $10^7$ particles/ml, $10^8$ particles/ml, $10^9$ particles/ml, $10^{10}$ particles/ml, and $10^{11}$ particles/ml), preferably from about $10^{10}$ particles/ml to about $10^{12}$ particles/ml, and will typically involve the intraocular administration of from about 0.1 μl to about 100 μl of such a pharmaceutical composition per eye. When the nucleic acid sequence is a plasmid, preferably about 0.5 ng to about 1000 μg of DNA is administered per eye. More preferably, about 0.1 μg to about 500 μg is administered per eye, even more preferably about 1 μg to about 100 μg of DNA is administered per eye. Most preferably, about 50 μg of DNA is administered per eye. Of course, other routes of administration may require smaller or larger doses to achieve a therapeutic effect. Any necessary variations in dosages and routes of administration can be determined by the ordinarily skilled artisan using routine techniques known in the art.

In some embodiments, it is advantageous to administer two or more (i.e., multiple) doses of the therapeutic factor or nucleic acid sequence encoding the therapeutic factor. The inventive method provides for multiple applications of the therapeutic factor to selectively induce apoptosis of endothelial cells associated with neovascularization, thereby prophylactically or therapeutically treating ocular neovascularization. For example, at least two applications of an expression vector comprising an exogenous nucleic acid, e.g., a nucleic acid sequence encoding the therapeutic factor, can be administered to the same eye. Preferably, the multiple doses are administered while retaining therapeutic factor concentrations above background levels. Also preferably, the ocular cell is contacted with two applications or more of the therapeutic factor or nucleic acid sequence encoding the therapeutic factor via direct administration to the eye within about 30 days or more. More preferably, two or more applications are administered to ocular cells of the same eye within about 90 days or more. However, three, four, five, six, or more doses can be administered in any time frame (e.g., 2, 7, 10, 14, 21, 28, 35, 42, 49, 56, 63, 70, 77, 85, or more days between doses) so long as ocular neovascularization is inhibited or ameliorated.

It also will be appreciated by one skilled in the art that a nucleic acid sequence encoding the therapeutic factor can be introduced ex vivo into ocular cells, previously removed from a given animal, in particular a human. Likewise, cells can be exposed to the therapeutic factor ex vivo, although this is less preferred. Such transduced autologous or homologous host cells, reintroduced into the animal or human, will express directly the therapeutic factor in vivo. One ex vivo therapeutic option involves the encapsidation of infected ocular cells into a biocompatible capsule, which can be implanted in the eye. Such cells need not be isolated from the patient, but can instead be isolated from another individual and implanted into the patient.

It will be appreciated that an expression vector comprising the nucleic acid sequence encoding the therapeutic factor, preferably an adenoviral vector comprising the nucleic acid sequence, can comprise multiple nucleic acid sequences encoding the therapeutic factor. For example, the expression vector can comprise multiple copies of the PEDF coding sequence, each copy operably linked to a different promoter or to identical promoters.

In addition, the nucleic acid sequence encoding the therapeutic factor can further comprise one or more other transgenes. By "transgene" is meant any nucleic acid that can be expressed in a cell. Desirably, the expression of the transgene is beneficial, e.g., prophylactically or therapeutically beneficial, to the ocular cell or eye. If the transgene confers a prophylactic or therapeutic benefit to the cell, the transgene can exert its effect at the level of RNA or protein. For example, the transgene can encode a peptide other than the therapeutic factor that can be employed in the treatment or study of a disorder, e.g., an ocular-related disorder. Alternatively, the transgene can encode an antisense molecule, a ribozyme, a protein that affects splicing or 3' processing (e.g., polyadenylation), or a protein that affects the level of expression of another gene within the cell (i.e., where gene expression is broadly considered to include all steps from initiation of transcription through production of a process protein), such as by mediating an altered rate of mRNA accumulation or transport or an alteration in post-transcriptional regulation. The transgene can encode a chimeric peptide for combination treatment of an ocular-related disorder. As discussed herein, different promoters have dissimilar levels and patterns of activity. One of ordinary skill in the art will appreciate the freedom to dictate the expression of different coding sequences through the use of multiple promoters. Alternatively, the multiple coding sequences can be operably linked to the same promoter to form a polycistronic element. The polycistronic element is transcribed into a single mRNA molecule when transduced into the ocular cell. Translation of the mRNA molecule is initiated at each coding sequence, thereby producing the multiple, separate peptides simultaneously.

An expression vector comprising the nucleic acid sequence encoding the therapeutic factor can comprise an additional therapeutic nucleic acid sequence, such as a nucleic acid sequence encoding a vessel maturation factor. Many ocular disorders involve leakage of blood products through vessels, which can cloud vision and induce an immune response within the layers of the eye. Vessel maturation factors reduce the amount of vascular leakage and, therefore, are useful in treating, for example, exudative ocular disorders. Vessel maturation factors include, but are not limited to, angiopoietins (Ang, e.g., Ang-1 and Ang-2), tumor necrosis factor-alpha (TNF-α), midkine (MK), COUP-TFII, and heparin-binding neurotrophic factor (HBNF, also known as heparin binding growth factor). A nucleotide sequence encoding an immunosuppressor also can be incorporated into the expression vector to reduce any inappropriate immune response within the eye as a result of an ocular-related disorder or the administration of the expression vector.

One or more additional nucleic acid sequences encoding an anti-angiogenic substance other than the therapeutic factor can be co-administered. As set forth above, an anti-angiogenic substance is any biological factor that prevents or ameliorates neovascularization. One of ordinary skill in the art will understand that the anti-angiogenic substance can effect partial or complete prevention and amelioration of angiogenesis to achieve a therapeutic effect. An anti-angiogenic substance includes, for instance, an anti-angiogenic factor, an anti-sense molecule specific for an angiogenic factor, a ribozyme, a receptor for an angiogenic factor, and an antibody that binds a receptor for an angiogenic factor.

A nucleic acid sequence encoding marker protein, such as green fluorescent protein or luciferase, can be present in an expression vector. Such marker proteins are useful in vector construction and determining vector migration. Marker proteins also can be used to determine points of injection or treated ocular tissues in order to efficiently space injections of a nucleic acid sequence or therapeutic factor to provide a widespread area of treatment, if desired. Alternatively, a nucleic acid sequence encoding a selection factor, which also is useful in vector construction protocols, can be part of the expression vector.

It should be appreciated that any of the therapeutic factors or nucleic acid sequences encoding therapeutic factors described herein can be altered from their native form to increase their therapeutic effect. For example, a cytoplasmic form of a therapeutic nucleic acid can be converted to a secreted form by incorporating a signal peptide into the encoded gene product. In addition, the therapeutic factor can be designed to be taken up by neighboring cells by fusion of the peptide with VP22. This allows an ocular cell comprising the therapeutic nucleic acid sequence to have a therapeutic effect on a number of ocular cells within the mammal. In other words, to contact an endothelial cell associated with neovascularization, a nucleic acid sequence encoding the therapeutic factor can transduce a cell in the vicinity of the neovascular process. Upon expression, a secretable therapeutic factor can be released into the environment of the target cell to exert its therapeutic effect.

The inventive method also can involve the co-administration of other pharmaceutically active compounds. By "co-administration" is meant administration before, concurrently with, e.g., in combination with the therapeutic factor or nucleic acid sequence encoding the therapeutic factor in the same formulation or in separate formulations, or after administration of the nucleic acid sequence encoding the therapeutic factor as described above. For example, factors that control inflammation, such as ibuprofen or steroids, can be co-administered to reduce swelling and inflammation associated with intraocular administration of the nucleic acid sequence encoding the therapeutic factor. Immunosuppressive agents can be co-administered to reduce inappropriate immune responses related to an ocular disorder or the practice of the inventive method. Anti-angiogenic factors, such as soluble growth factor receptors, growth factor antagonists, e.g., angiotensin, and the like can also be co-administered, as well as neurotrophic factors. Similarly, vitamins and minerals, anti-oxidants, and micronutrients can be co-administered. Antibiotics, i.e., microbicides and fungicides, can be co-administered to reduce the risk of infection associated with ocular procedures and some ocular-related disorders.

While the invention is particularly suited for the treatment of disorders involving angiogenesis in the eye, it will be appreciated that neovascularization is linked to other disorders associated with other regions of the body. Indeed, as most angiogenesis-related diseases involve uncontrolled or abnormal growth of new blood vessels, the therapeutic factor or nucleic acid sequence encoding the therapeutic factor is appropriate for use in the prophylactic or therapeutic treatment of neovascularization-related disorders in other tissues. Accordingly, the invention further comprises a method of prophylactically or therapeutically treating a tissue for abnormal or uncontrolled neovascularization (i.e., neovascularization having a detrimental effect), wherein the method comprises directly administering a therapeutic factor or a nucleic acid sequence encoding a therapeutic factor, which is expressed to produce the therapeutic factor, to a target tissue to selectively induce apoptosis of endothelial cells associated with neovascularization of the target tissue, such that neovascularization is treated prophylactically or therapeutically.

For example, the therapeutic factor or the nucleic acid sequence encoding the therapeutic factor can be delivered to tissues including, for example, muscle tissue, joint tissue, skin, and tumor tissue to therapeutically or prophylactically treat neovascularization. For example, skin disorders including psoriasis, scleroderma, and hair loss involve neovascular complications. Some forms of arthritis stem from uncontrolled angiogenesis in the joints. In addition, tumor formation and growth are dependent, in part, on the formation of new blood vessels to deliver nutrients and oxygen to the tumor. These ailments can be controlled by treating or inhibiting, at least in part, vascular proliferation.

The dosages of therapeutic factor or nucleic acid sequence encoding the therapeutic factor, compositions, formulations, and other considerations described above are appropriate for the prophylactic or therapeutic treatment of neovascularization-related disorders in regions of the body other than the eye. Local or systemic delivery of the therapeutic factor or nucleic acid sequence encoding the therapeutic factor can be accomplished by administration comprising application or instillation of the formulation into body cavities, inhalation or insufflation of an aerosol, or by parenteral introduction, comprising intramuscular, intravenous, peritoneal, subcutaneous, intraarterial, intraocular, and intradermal administration, as well as topical administration. However, direct administration involving injection or topical application directly to the target tissue wherein neovascularization is to be modulated as described in, for example, International Patent Application WO 98/32859, is most preferred. Of course, the routes of administration discussed herein are merely exemplary. The present inventive methods are not dependent on the particular route of administration or dose administered.

EXAMPLES

The following examples further illustrate the invention but, of course, should not be construed as in any way limiting its scope.

Example 1

This example illustrates a preferred method of obtaining expression of a factor comprising both anti-angiogenic and neurotrophic activity from an adenoviral vector in in vivo retina.

An adenoviral vector deficient in one or more essential gene functions of the E1, E3, and E4 regions of the adenoviral genome and comprising a PEDF gene (AdPEDF) is preferably constructed as set forth in International Patent Application WO 99/15686 (McVey et al.). However, the method of the invention is not dependent on the method of vector construction employed, and previously described methods of vector construction are also suitable.

Several in vivo models of ocular neovascularization are available. Neovascularization of the retina is obtained in, for example, neonatal animals, i.e., neonatal mice, by exposing the mice to hypoxic conditions shortly after birth. Several days later, the neonatal mice are exposed to standard atmospheric conditions, resulting in ischemia-induced neovascularization of the retina.

AdPEDF is administered to the right eye of at least 12 day old mice anesthetized with, for example, ketamine or a combination of ketamine and xylazine via intravitreal injection. Injections are performed by forming an entrance site in the posterior portion of the eye and administering approximately 0.1-5.0 μl of a pharmaceutical composition comprising AdPEDF. In most instances, an injection of the expression vector will be administered to only one eye, while the remaining eye serves as a control. The mice are sacrificed at various time points after administration of the pharmaceutical composition to determine the extent and duration of PEDF expression in the retina. The right and left eyes of each animal are enucleated and either fixed for histological analysis or prepared for PEDF expression analysis. Detection of PEDF DNA, PEDF RNA, or PEDF protein can be accomplished using methods well known in the art, such as PCR and blotting techniques (see, for example, Sambrook et al., supra).

To determine the effect of PEDF on neovascularization in vivo in, for example, a human, indirect opthalmoscopy of the retina is ideal. Stereophotographs are useful in detecting extensive neovascularization, but not appropriate for detecting subtle lesions. Apoptosis of endothelial cells can be detected using the TUNEL assay. Comparision of the level of apotosis in cells associated with new blood vessel growth can be compared to the level of apoptosis (if any) in cells associated with pre-existing blood vessels.

Example 2

This example demonstrates the utility of adenoviral vectors to deliver multiple doses of an exogenous nucleic acid to the eye.

Adenoviral vectors comprising the luciferase gene (Ad.L) or control adenoviral vectors comprising no transgene (Ad.null) were injected into the intravitreal space of C57BL6 mouse eyes (Day 0). One day following injection of the adenoviral vectors (Day 1), eyes infected with Ad.L were enucleated and frozen ($1^{st}$ administration). The eyes infected with Ad.null were divided into three groups. In Group I, Ad.L vectors were injected into the intravitreal space of the eye at Day 14 (fourteen days following the initial dose of Ad.null). Group I eyes were enucleated and frozen the day following the second administration of adenoviral vectors (Day 15, $2^{nd}$ administration). Group II eyes were injected intravitreally with Ad.null at Day 14, and injected intravitreally with Ad.L vectors four weeks following the initial injection with Ad.null (Day 28, $3^{rd}$ administration). The eyes were then enucleated and frozen the day after the third administration of adenoviral vector. Group III eyes were injected intravitreally with Ad.null at Day 14 and Day 28, and injected with Ad.L vectors six weeks following the initial injection with Ad.null (Day 42, $4^{th}$ administration). The eyes were then enucleated and frozen the day after the fourth administration of adenoviral vector. Luciferase assays were performed on the eye samples to determine the efficiency of infection and gene expression associated with multiple dosing of the vectors.

Luciferase expression in ocular cells after the $1^{st}$ and $2^{nd}$ administration of adenoviral vector was substantially equivalent. In other words, no loss of gene expression was detected following two administrations of the gene transfer vector. Gene expression from the $3^{rd}$ administration of adenoviral vector was between 10- and 100-fold reduced compared to gene expression from the $1^{st}$ administration and the $2^{nd}$ administration, but was still above background levels (e.g., as detected in cells transduced with Ad.null). Gene expression from the $4^{th}$ administration of adenoviral vector was reduced approximately 3- to 10-fold compared to the gene expression observed following the $3^{rd}$ administration. However, the level of gene expression following the $4^{th}$ administration was above background levels.

This example demonstrates the feasibility of performing multiple applications of adenoviral vectors to the eye in order to obtain expression of an exogenous nucleic acid in ocular cells.

Example 3

This example demonstrates the ability of an expression vector comprising a nucleic acid sequence encoding a factor comprising both anti-angiogenic and neurotrophic properties to inhibit choroidal neovascularization (CNV).

Replication-deficient (E1-/E3-deficient) adenoviral vectors (AdPEDF.10) comprising the coding sequence for PEDF operably linked to the CMV immediate early promoter were constructed using standard techniques. A null version of the vector (AdNull.10), which did not comprise the PEDF coding sequence, was also constructed.

Adult C57BL/6 mice were injected intravitreously with AdNull.10 or AdPEDF.10 using a Harvard pump microinjection apparatus and pulled glass micropipettes. Each eye was injected intravitreously with 1 μl of vehicle containing $10^9$ particles of virus. Alternatively, each eye was injected subretinally with $10^8$ particles of virus suspended in 1 μl of vehicle. Five days post-injection, mice were anesthetized with ketamine hydrochloride (100 mg/kg body weight). Tropicamide (1%) was utilized to dilate the pupils prior to rupture of Bruch's membrane by diode laser photocoagulation. Rupture of Bruch's membrane is known to induce neovascularization of the choroid.

Fourteen days following laser-induced rupture of Bruch's membrane, choroidal flat mounts (described in Edelman et al., *Invest. Ophthalol. Vis. Sci.*, 41, S834 (2000)) were prepared to observe the degree of neovascularization of the choroidal membrane. Briefly, eyes were removed from the subjects and fixed in phosphate-buffered formalin. The cornea, lens, and retina were removed from the eyecup, and the eyecup was flat-mounted. Flat mounts were then examined by fluorescence microscopy and images were digitized using a 3 color CCD video camera (IK-TU40A, Toshiba, Tokyo, Japan) for computer image analysis.

Large areas of neovascularization were observed in uninjected eyes and eyes receiving AdNull.10. Eyes injected with AdPEDF.10 subretinally or intravitreously showed smaller regions of neovascularization, as compared to the controls, using computerized image analysis.

These results illustrate the ability of the inventive method to inhibit ocular neovascularization, particularly choroidal neovascularization (CNV), in a clinically animal relevant model.

Example 4

This example demonstrates the ability of an expression vector comprising a nucleic acid sequence encoding a factor comprising both anti-angiogenic and neurotrophic properties to inhibit ischemia-induced retinal neovascularization.

Replication-deficient adenoviral vectors comprising the coding sequence for PEDF operably linked to the CMV immediate early promoter were constructed using standard techniques. E1-/E3-/E4-deficient vectors encoding PEDF (AdPEDF.11) and a null version of the vector (AdNull.11), which did not comprise the PEDF coding sequence, were constructed.

Ischemic retinopathy was produced in adult C57BL/6 mice as previously described (see, for example, Smith et al., *Invest. Opthalmol. Vis. Sci.*, 35, 101 (1994)). In particular, seven day old mice were exposed to an atmosphere of 75+/−3% oxygen for five days. When the mice were ten days old, i.e., after three days exposure to the aforementioned oxygen atmosphere, the mice were injected intravitreously with $10^9$ particles of AdPEDF.11 or AdNull.11, returned to the oxygen atmosphere for two more days, and then returned to room atmosphere. When the mice were seventeen days old, i.e., five days later, the mice were sacrificed, and their eyes were rapidly removed and frozen in optimum cutting temperature embedding compound (OCT; Miles Diagnostics, Elkhart, Ind.).

To detect neovascularization, the eyes were sectioned on slides and histochemically stained with biotinylated griffonia simplicifolia lectin B4 (GSA, Vector Laboratories, Burlingame, Calif.). The slides were incubated in methanol/$H_2O_2$ for 10 minutes at 4° C., washed with 0.05 M Tris-buffered saline, pH 7.6 (TBS), and incubated for 30 minutes in 10% normal porcine serum. The slides were then incubated for two hours with biotinylated GSA, rinsed with TBS, and incubated with avidin-coupled alkaline phosphatase (Vector Laboratories) for 45 minutes. After a 10 minute wash with TBS, the slides were incubated with Histomark Red. GSA-stained, 10 μm serial sections were examined using an Axioskop microscope. Images were digitized using a 3 color CCD video camera (IK-TU40A, Toshiba, Tokyo, Japan) for computer image analysis.

Extensive retinal neovascularization was detected in eyes not injected with any expression vector. Eyes injected with AdNull.11 showed less neovascularization than uninjected eyes, but significantly more neovascularization of the retina than eyes injected with AdPEDF.11. Eyes injected with AdPEDF.11 comprised the least amount of neovascularization.

These results clearly demonstrate the ability of the inventive method to inhibit an ocular-related disorder, particularly ischemia-induced retinal neovascularization, in a clinically relevant animal model.

Example 5

This example illustrates the ability of the inventive method to promote regression of ocular neovascularization. This example further demonstrates the induction of apoptosis in endothelial cells associated with neovascularization by a therapeutic factor with no damage to existing vasculature.

AdPEDF.11, i.e., E1-/E3-/E4-deficient adenoviral vectors comprising the coding sequences for PEDF operably linked to the CMV immediate early promoter were constructed as previously described in Example 4. AdNull.11 adenoviral vectors that do not express transgene products also were constructed as described in Example 4.

The effect of a therapeutic factor, PEDF, on CNV induced by exposure of a mouse eye to laser was examined. Briefly, adult C57BL/6 mice were anesthetized with ketamine hydrochloride (100 mg/kg body weight), pupils were dilated with 1% tropicamide, and diode laser photocoagulation was used to rupture Bruch's membrane at 3 locations in each eye of each mouse as previously described herein. Laser photocoagulation (532 nm wavelength, 100 μm spot size, 0.1 seconds duration, and 120 mW intensity) was delivered using the slit lamp delivery system, and a hand-held cover slide as a contact lens. Burns were performed in the 9, 12, and 3 o'clock positions 2-3 disc diameters from the optic nerve. Production of a vaporization bubble at the time of laser, which indicates rupture of Bruch's membrane, is an important factor in obtaining CNV, so only burns in which a bubble was produced were included in the study.

Two weeks after rupture of Bruch's membrane, a cohort of mice was sacrificed, and the baseline amount of choroidal neovascularization was measured at each rupture site as described below. The remainder of the mice received an intravitreous injection of $10^9$ particles or a subretinal injection of $10^8$ particles of AdNull.11 or AdPEDF.11 in each eye. Intravitreous injections were done with a Harvard pump microinjection apparatus and pulled glass micropipets. Each micropipet was calibrated to deliver 1 μl of vehicle containing $10^9$ or $10^8$ particles upon depression of a foot switch. The mice were anesthetized, pupils were dilated, and under a dissecting microscope, the sharpened tip of the micropipet was passed through the sclera just behind the limbus into the vitreous cavity, and the foot switch was depressed. Subretinal injections were performed using a condensing lens system on the dissecting microscope, which allowed visualization of the retina during the injection. The pipet tip was passed through the sclera posterior to the limbus and was positioned just above the retina. Depression of the foot switch caused the jet of injection fluid to penetrate the retina, resulting in fairly uniform blebs that confirmed that the vector had been deposited in the subretinal space.

To detect choroidal neovascularization, the area of choroidal neovascularization at each rupture site was measured in choroidal flat mounts ten days after vector injection. Mice were anesthetized and perfused with 1 ml of phosphate-buffered saline containing 50 mg/ml of fluorescein-labeled dextran ($2 \times 10^6$ average MW, Sigma, St. Louis, Mo.). The eyes were removed and fixed for 1 hour in 10% phosphate-buffered formalin. The cornea and lens were removed, and the entire retina was carefully dissected from the eyecup. Radial cuts (4-7 cuts, average 5 cuts) were made from the edge to the equator, and the eyecup was flat mounted in Aquamount with the sclera facing down. Flat mounts were examined by fluorescence microscopy on an Axioskop microscope (Zeiss, Thornwood, N.Y.), and images were digitized using a 3 color CCD video camera (IK-TU40A, Toshiba, Tokyo, Japan) and a frame grabber. Image-Pro Plus software (Media Cybernetics, Silver Spring, Md.) was used to measure the total area of hyperfluorescence associated with each burn, corresponding to the total fibrovascular scar. The areas within each eye were averaged to give one experimental value, and mean values were calculated for each treatment group and compared by Student's unpaired t-test.

Fourteen or 24 days after laser treatment in adult C57BL/6 mice, there was extensive choroidal neovascularization at sites of rupture of Bruch's membrane. Mice that received an intravitreous injection of $10^9$ particles of AdNull.11 fourteen days after laser treatment, and were sacrificed 10 days later, had large areas of choroidal neovascularization at the sites of rupture of Bruch's membrane that looked very similar to those seen in uninjected mice. The same was true for mice that received a subretinal injection of $10^8$ particles of AdNull.11 fourteen days after laser treatment and were sacrificed 10 days later. This was true regardless of whether the rupture site was outside the region of retina that was detached by the subretinal injection or within the area of the bleb.

In contrast, mice that received an intravitreous injection of $10^9$ particles of AdPEDF.11 fourteen days after laser treatment, and were sacrificed 10 days later, had smaller areas of choroidal neovascularization than AdNull.11-injected or uninjected mice. Moreover, the morphology of the hyperfluorescent area was unusual in that the borders were irregular and there was prominent surrounding hyperpigmentation. The appearance is consistent with regression of choroidal neovascularization, leaving hyperpigmentation in the region in which involution of neovascularization occurred.

Hyperpigmentation surrounding an irregular area of hyperfluorescence was not the only morphology that suggested regression in treated mice. In a lesion detected 24 days after rupture of Bruch's membrane in a mouse that received a subretinal injection of $10^8$ particles of AdPEDF.11 fourteen days after laser treatment, the area of hyperfluorescence is smaller than those seen in AdNull.11-injected or uninjected mice, and it consists of a few relatively large vessels and no small vessels. A possible explanation is that the small vessels regressed, leaving only a few larger vessels. This lesion was located within the subretinal bleb caused by the subretinal injection of AdPEDF.11. A second lesion was studied from a mouse that was given a subretinal injection of $10^8$ particles of AdPEDF.11 fourteen days after laser treatment, but the rupture site was outside the region of the bleb. Compared to lesions in Ad.Null-injected or uninjected eyes, the second lesion was smaller and had a morphology consisting of a small region of hyperfluorescence surrounded by hyperpigmentation, similar to that of lesions seen in many eyes that received an intravitreous injection of AdPEDF.11.

Measurement of the areas of choroidal neovascularization at rupture sites showed that eyes that received either an intravitreous or subretinal injection of AdPEDF.11 on day 14 after laser treatment had significantly less neovascularization on day 24 than eyes injected with AdNull.11 or uninjected eyes. Eyes that received a subretinal injection of AdPEDF.11 also had significantly less neovascularization than the baseline amount seen at day 14, suggesting that regression of choroidal neovascularization had occurred.

Apoptotic cells were detected by TdT-dUTP terminal nick end-labeling (TUNEL). Ten days after the intraocular injection of vector, and 24 days after rupture of Bruch's membrane, the eyes were rapidly removed and frozen in optimum cutting temperature embedding compound (OCT; Miles Diagnostics, Ellhart, Ind.). Frozen serial sections (10 μm) were cut through the entire extent of each burn. Sections were fixed in 4% paraformaldehyde for 20 minutes at room temperature and stained with the in situ cell death detection kit (Roche Diagnostics, Indianapolis, Ind.) according to the manufacturer's instructions. The sections were also histochemically stained with biotinylated *Griffonia simplicifolia* lectin B4 (GSA, Vector Laboratories, Burlingame, Calif.) which selectively binds vascular cells. After TUNEL staining, coverslips were removed, and the slides were incubated in methanol/$H_2O_2$ for 10 minutes at 4° C., washed with 0.05 M Tris-buffered saline, pH 7.6 (TBS), and incubated for 30 minutes in 10% normal porcine serum. Slides were incubated 2 hours at room temperature with biotinylated GSA, and after rinsing with 0.05M TBS, they were incubated with avidin coupled to alkaline phosphatase (Vector Laboratories) for 30 minutes at room temperature. After being washed for 10 minutes with 0.05 M TBS, slides were incubated with Histomark Red (Kirkegaard and Perry) to give a red reaction product that is distinguishable from melanin. Some slides were counterstained with Contrast Blue (Kirkegaard and Perry).

Fourteen days after laser-induced rupture of Bruch's membrane, mice received no injection, an intravitreous injection of $10^9$ particles of AdNull.11 or AdPEDF.11, or a subretinal injection of $10^8$ particles of AdNull.11 or AdPEDF.11. Ten days later, the mice were sacrificed, and ocular sections were labeled with GSA lectin. TUNEL staining was done on adjacent sections, or sections were double-labeled with GSA and TUNEL. Uninjected eyes showed a few TUNEL-stained cells in the retina overlying laser-induced choroidal neovascularization, but none within the choroidal neovascularization. The same was true for eyes that received a subretinal injection of vehicle alone or an intravitreous injection of AdNull.11. In contrast, TUNEL staining in eyes that received an intravitreous injection of AdPEDF.11 showed a few labeled cells within choroidal neovascular lesions, and eyes that received a subretinal injection of AdPEDF.11 showed numerous labeled cells in choroidal neovascular lesions that also stained with GSA, indicating that they were dying vascular cells. There was also prominent TUNEL staining of photoreceptor cells in regions of retina that had been detached by subretinal injection of AdPEDF.11. Eyes that had received subretinal injection of AdNull.11 also showed prominent TUNEL labeling of photoreceptors in areas of retina that had been detached by the injection, but no staining of cells in choroidal neovascular lesions. These results suggest that the death of retinal neurons is attributable to the adenoviral vector, and apoptosis of vascular cells in choroidal neovascular lesions is due to PEDF. In AdPEDF.11-injected eyes, many TUNEL-stained cells within the choroidal neovascularization and the feeder vessels from the underlying choroid were observed, but no TUNEL staining of the retinal vascular cells which were not participating in the neovascularization was detected. Also, choroidal vascular cells in areas not underlying choroidal neovascularization showed no TUNEL staining.

These results demonstrate that direct administration of a nucleic acid sequence encoding a therapeutic factor, which selectively induces apoptosis in endothelial cells associated with neovascularization, therapeutically treats neovascularization in a clinically-relevant animal model.

Example 6

This example illustrates the ability of the inventive method to promote regression of retinal neovascularization.

AdPEDF.11, i.e., E1-/E3-/E4-deficient adenoviral vectors comprising the coding sequences for PEDF operably linked to the cytomegalovirus (CMV) immediate early promoter, were constructed as previously described in Example 4. AdNull.11 adenoviral vectors that do not express transgene products also were constructed as described in Example.

Transgenic mice with VEGF expression driven by the rhodopsin promoter (rho/VEGF mice) develop subretinal neovascularization due to expression of VEGF in photoreceptors beginning at about six days after birth and, therefore, present an ideal model for determining the effect of a therapeutic factor, e.g., PEDF, on retinal neovascularization. At 21 days after birth, a cohort of transgene-positive mice was sacrificed, and the amount of neovascularization in each retina was measured as described below. The remainder of the mice received no injection or an intravitreous injection of $10^9$ particles of AdNull.11 or AdPEDF.11. At 28 days after birth, the mice were sacrificed and the amount of subretinal neovascularization was quantified as previously described. Briefly, mice were anesthetized and perfused with 1 ml of phosphate-buffered saline containing 50 mg/ml of fluorescein-labeled dextran ($2 \times 10^6$ average MW, Sigma, St. Louis, Mo.). The eyes were removed and fixed for 1 hour in 10% phosphate-buffered formalin. The cornea and lens were removed, and the entire retina was carefully dissected from the eyecup, radially cut from the edge of the retina to the equator in all 4 quadrants, and flat-mounted in Aquamount with photoreceptors facing upward. The retinas were examined by fluorescence microscopy at 200× magnification, which provides a narrow depth of field so that, when focusing on neovascularization on the outer surface of the retina, the remainder of the retinal vessels are out-of-focus allowing easy delineation of the neovascularization. The outer edge of the retina, which corresponds to the subretinal space in vivo, is easily identified and therefore there is standardization of focal plane from slide to slide. Images were digitized using a 3 CCD color video camera and a frame grabber. Image-Pro Plus was used to identify each of the lesions, calculate the number in each retina, delineate the area of each lesion, and delineate the total area of neovascularization per retina.

In rho/VEGF transgenic mice, expression of VEGF in photoreceptors begins at about six days after birth, increases to a steady-state level by about 14 days after birth, and continues at that level throughout adulthood. The total area of subretinal neovascularization per retina steadily increases between 18 days after birth and 45 days after birth, the oldest age examined. Transgenics that received an intravitreous injection of $10^9$ particles of AdNull.11 on day 21 after birth, had extensive neovascularization at 28 days after birth, but it appeared somewhat less than that seen in uninjected mice 28 days after birth. Transgenics that received an intravitreous injection of $10^9$ particles of AdPEDF.11 at 21 days after birth, had much less neovascularization than uninjected mice 28 days after birth; there were RPE cells present, but almost no hyperfluorescence associated with the RPE cells. Neovascularization had been present and regressed, leaving RPE cells without hyperfluorescence in their wake, as supported by quantitative analysis. The total area of neovascularization per retina was significantly greater at 28 days after birth compared to uninjected mice at 21 days after birth. Mice that received an intravitreous injection of $10^9$ particles of AdNull.11 at 21 days after birth and were then sacrificed at 28 days after birth showed less neovascularization than uninjected mice 28 days after birth, but no significant difference from uninjected mice at 21 days after birth. This observation reflects that the vector itself has some antiangiogenic activity in the transgenic model, as was shown in a previous study. However, mice that received an intravitreous injection of $10^9$ particles of AdPEDF.11 at 21 days after birth, had less neovascularization at 28 days after birth than AdNull.11-injected mice at 28 days after birth or uninjected mice at 21 days after birth. This confirms that intraocular expression of PEDF caused regression of subretinal neovascularization in rho/VEGF transgenic mice.

These results demonstrate that direct administration of a nucleic acid sequence encoding a therapeutic factor, e.g., PEDF, and expression of the nucleic acid sequence in the eye, promotes regression of neovascularization, in particular subretinal neovascularization.

Example 7

This example illustrates that periocular delivery of a nucleic acid encoding a therapeutic factor, e.g., PEDF, inhibits choroidal neovascularization.

Bruch's membrane was ruptured with laser photocoagulation at 3 locations in each eye of adult C57BL/6 mice. Immediately after laser treatment, mice were given a periocular injection of 3 μl of a composition containing $5 \times 10^9$ particles of AdPEDF.11 (as described in Example 5) in one eye and $5 \times 10^9$ particles of Adnull.11 (as also described in Example 5) in the fellow eye. After two weeks, mice were perfused with fluorescein-labeled dextran, and the area of CNV at each rupture site was measured on choroidal flat mounts by computerized image analysis as described above.

The mean area of CNV at Bruch's membrane rupture sites was significantly reduced in eyes given a periocular injection of AdPEDF.11 compared to fellow eyes given a periocular injection of Adnull.11. Thus, a nucleic acid sequence encoding a therapeutic factor delivered periocularly inhibits neovascularization of the eye.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of therapeutically treating choroidal neovascularization in a mammal, wherein the method comprises periocularly injecting an adenoviral vector comprising a nucleic acid sequence encoding pigment epithelium-derived factor operatively linked to a cytomegalovirus (CMV) promoter, which nucleic acid sequence is expressed to produce pigment epithelium-derived factor, to the eye of a mammal to selectively induce apoptosis of endothelial cells associated with neovascularization of the choroid, such that choroidal neovascularization is treated therapeutically in the mammal.

2. The method of claim 1, wherein the adenoviral vector is replication deficient.

3. The method of claim 2, wherein the adenoviral vector is deficient in one or more gene functions of the E1 region required for viral replication.

4. The method of claim 3, wherein the adenoviral vector is deficient in one or more gene functions of the E4 region required for viral replication.

5. The method of claim 4, wherein the adenoviral vector is deficient in one or more gene functions of the E3 region of the adenoviral genome.

6. The method of claim 3, wherein the adenoviral vector is deficient in one or more gene functions of the E3 region of the adenoviral genome.

7. The method of claim 2, wherein the adenoviral vector is deficient in one or more gene functions of the E4 region required for viral replication.

8. The method of claim 7, wherein the adenoviral vector is deficient in all gene functions required for viral replication.

9. The method of claim 7, wherein the adenoviral vector is deficient in one or more gene functions of the E3 region of the adenoviral genome.

10. The method of claim 1, wherein the adenoviral vector is deficient in one or more gene functions of the E3 region of the adenoviral genome.

* * * * *